United States Patent
Schmidt et al.

(10) Patent No.: US 6,278,037 B1
(45) Date of Patent: Aug. 21, 2001

(54) ABSORBENT ARTICLE HAVING IMPROVED COMFORT DURING USE BY IMPROVED FIT EVEN WHEN LOADED AND IMPROVED REWET PERFORMANCE

(75) Inventors: Mattias Schmidt, Idstein; Gianfranco Palumbo, Bad Homburg; Bruno Johannes Ehrnsperger, Frankfurt, all of (DE); Frank Neumann, Cincinnati, OH (US); Gary D. Lavon, Oberursel (DE); Gerald A. Young, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/381,927

(22) PCT Filed: Mar. 27, 1997

(86) PCT No.: PCT/US97/05048

§ 371 Date: Nov. 5, 1999

§ 102(e) Date: Nov. 5, 1999

(87) PCT Pub. No.: WO98/43579

PCT Pub. Date: Oct. 8, 1998

(51) Int. Cl.[7] .................................................... A61F 13/15
(52) U.S. Cl. ........................... 604/369; 604/367; 604/378
(58) Field of Search .................................. 604/358, 367, 604/369, 378

(56) References Cited

U.S. PATENT DOCUMENTS

| | | | |
|---|---|---|---|
| 3,860,003 | * | 1/1975 | Buell .................................... 128/284 |
| 4,994,037 | | 2/1991 | Bernardin ............................. 604/368 |
| 5,098,423 | | 3/1992 | Pieniak et al. .................... 604/385.1 |
| 5,554,144 | * | 9/1996 | Roe et al. ............................. 604/385 |
| 5,632,737 | * | 5/1997 | Stone et al. .......................... 604/358 |
| 6,022,818 | * | 2/2000 | Welchel et al. ..................... 442/384 |
| 6,085,579 | * | 7/2000 | Herrlein .................................. 73/73 |
| 6,107,537 | * | 8/2000 | Elder et al. .......................... 604/364 |

FOREIGN PATENT DOCUMENTS

| | | | | |
|---|---|---|---|---|
| 0 039 974 A1 | * | 11/1981 | (EP) | ................................... 604/358 |
| 0 278 601 A2 | * | 8/1988 | (EP) | ................................... 604/358 |
| 0 374 260 A1 | * | 6/1990 | (EP) | ................................... 604/358 |
| WO 90/14815 | * | 12/1990 | (EP) | ................................... 604/358 |
| 0 422 504 A2 | * | 4/1991 | (EP) | ................................... 604/358 |
| WO 91/11978 | * | 8/1991 | (EP) | ................................... 604/358 |
| WO 91/15177 | * | 10/1991 | (EP) | ................................... 604/358 |
| WO 92/11831 | * | 7/1992 | (EP) | ................................... 604/358 |
| WO 92/18171 | * | 10/1992 | (EP) | ................................... 604/358 |
| 0 539 703 A1 | * | 5/1993 | (EP) | ................................... 604/358 |
| 0 631 768 B1 | | 1/1995 | (EP) . | |
| 0 631 768 A1 | * | 1/1995 | (EP) | ................................... 604/358 |
| 0 640 330 A1 | * | 3/1995 | (EP) | ................................... 604/358 |
| 0 422 504 B1 | | 6/1995 | (EP) . | |
| 0 797 968 A1 | * | 10/1997 | (EP) | ................................... 604/358 |
| WO 98/58615 | * | 12/1998 | (EP) | ................................... 604/358 |
| WO 93/16669 | | 9/1993 | (WO) . | |
| WO 93/21877 | | 11/1993 | (WO) . | |

* cited by examiner

Primary Examiner—John G. Weiss
Assistant Examiner—Mike Bogart
(74) Attorney, Agent, or Firm—Jay A. Krebs; David M. Weirich; Ken K. Patel

(57) ABSTRACT

Absorbent article comprising an absorbent core with a crotch region and at least one waist region, whereby said crotch region has a lower ultimate fluid storage capability than said at least one waist region. The article further has an improved fluid handling performance in particular a low rewet value for minimizing skin hydration during use, such as measured by the post acquisition collagen rewet method value not exceeding 180 mg.

24 Claims, 6 Drawing Sheets

ABSORBENT ARTICLE HAVING IMPROVED COMFORT DURING USE BY IMPROVED FIT EVEN WHEN LOADED AND IMPROVED REWET PERFORMANCE

FIELD OF THE INVENTION

The present invention relates to absorbent articles which are primarily designed to receive and retain bodily discharges such as—and foremost—urine. Such articles are disposable hygiene articles like baby diapers, training pants, Adult incontinence Articles and the like.

BACKGROUND OF THE INVENTION

Absorbent Articles for receiving and retaining bodily discharges such as urine or feces such as disposable diapers, training pants, adult incontinence articles are well known in the art, and significant effort has been spent against improving their performance. Such improvements generally aim at addressing the primary function of such articles, namely retaining body fluids, but also at minimizing the negatives associated with wearing such articles by increasing the comfort of the wearer.

Such improvements can mostly be classified to primarily fall within either of two categories: primarily relating to "core technology", i.e. "absorbency" in the broad sense of the word, or primarily relating to "chassis technology".

The first addresses how to pick up and retain the body waste (generally in some state of fluidity) in an "absorbent (or core) structure", whereby the waste material is acquired by the article (picked up) and then stored (retained), with potentially an additional step of distribution (in particular of urine) in between.

The second category deals—generally—with the so called "chassis elements", namely containing the body waste "within the confinement of the article"

by separating the absorbent (core structure) and the outside, i.e. wearers garments, etc., by using an impermeable "backsheet";

or by preventing bodily exudates from escaping through the space between the absorbent article and the body of the wearer, such as by elasticized gatherings at leg and waist openings.

This also deals with enabling application of the article to the wearer—such as by providing closure means such as tapes, and maintaining the article on the wearer, such as through belt like arrangements often integrated into the application means.

With this terminology, "comfort" for the wearer is at present predominantly being addressed by improving chassis elements, such as by adopting the chassis elements of the diaper to provide good "fit" of the article and to be soft and cushioning.

In PCT application WO 93/16669 (Alemany) or PCT application WO 93/21877 (Richardson) disposable diapers are described, whereby the comfort of the wearer is enhanced by introducing elasticised features such as allowing better body conformity even if the wearer is moving.

When considering the impact of cores on comfort, the general approach is to do so by using soft, non chafing materials for topsheets or minimizing the thickness and/or volume of the dry article, preferably while maintaining softness of such cores. Recently, attempts have been made to also adopt the form and shape of the absorbent structure to allow good fit.

Since so called superabsorbent materials (or hydrogel forming materials) have found wide spread application in disposable absorbent articles, a number of marketed products—such as PAMPERS as sold by The Procter & Gamble Co. or HUGGIES as sold by Kimberly-Clark Corp. in various countries—underwent a remarkable reduction in the thickness of the products.

U.S. Pat. No. 5,098,423 (Pieniak) describes disposable diapers, which attempts to address various "comfort" aspects by providing "low dry bulk" structures, claiming that not only the dry thickness of the structure is relevant, but also other dimensions like the cross-sectional area of the core in the crotch region;
the compressibility of the article in the crotch region and the resulting thickness of the article after folding;
size of the "impact zone of the article";
distance of the (leg) elastic members of the article.

Further, an "Absorbency Efficiency Index" is described, by relating an amount of fluid, which should be picked up by the crotch region, to the volume of the dry core. The objective of this parameter is to allow designing towards high absorbency characteristics, capacity, in the crotch region. Thus is still a key objective to also absorb large amounts of urine in the crotch area, which, however, inevitably reduces comfort after loading significantly. This issue becomes even more pronounced with further improving the performance of absorbent articles yielding absorbent articles providing significantly better fluid handling performance, and hence an increase in overall wearing time and amount of fluid contained in such articles before being removed.

In U.S. Pat. No. 4,994,037 (Bemardin) absorbent articles are described, having a "reversed capacity profile". Therein, the ultimate storage capacity is positioned away from the crotch region. However, the disclosed designs for absorbent articles do not consider the fit requirement of fitting well between the legs of the wearer, nor the fluid handling requirements, such as achieving appropriate skin dryness and fluid acquisition. While these designs arrange the capacity away from the loading point, they were not concerned with how to effectively achieve the fluid transport to these storage regions.

Hence it is an object of the present invention to provide absorbent articles having an improved fit also when being loaded, together with good fluid handling performance, especially having a good rewet performance.

It is a further object of the present invention to achieve this by selectively placing ultimate storage capacity away from the crotch region.

It is a further object of the present invention to provide this feature without detrimentally affecting the fit when dry by providing designs with low bulk in the article crotch region.

It is a further object of the invention to achieve this by using distribution materials having high flux wicking properties, It is a further object of the invention to achieve this by using Superabsorbent polymers.

It is a further object of the invention, to achieve this by using porous absorbent materials, such as made by HIPE polymerisation.

BRIEF DESCRIPTION OF THE DRAWINGS

FIG. 3b is showing a somle holder fot the test set up shown in FIG. 3a.

DETAILED DESCRIPTION

Absorbent Articles—General

As used herein, the term "absorbent articles" refers to devices which absorb and contain body exudates, and, more specifically, refers to devices which are placed against or in proximity to the body of the wearer to absorb and contain the various exudates discharged from the body, primarily urine.

The term "disposable" is used herein to describe absorbent articles which are not intended to be laundered or otherwise restored or reused as an absorbent article (i.e., they are intended to be discarded after use and, preferably, to be recycled, composted or otherwise disposed of in an environmentally compatible manner).

An absorbent article generally comprises:

an absorbent core or core structure (which may consist of sub-structures);

a fluid pervious topsheet;

a fluid impervious backsheet;

optionally further features like closure elements or elastification.

Figure 1:
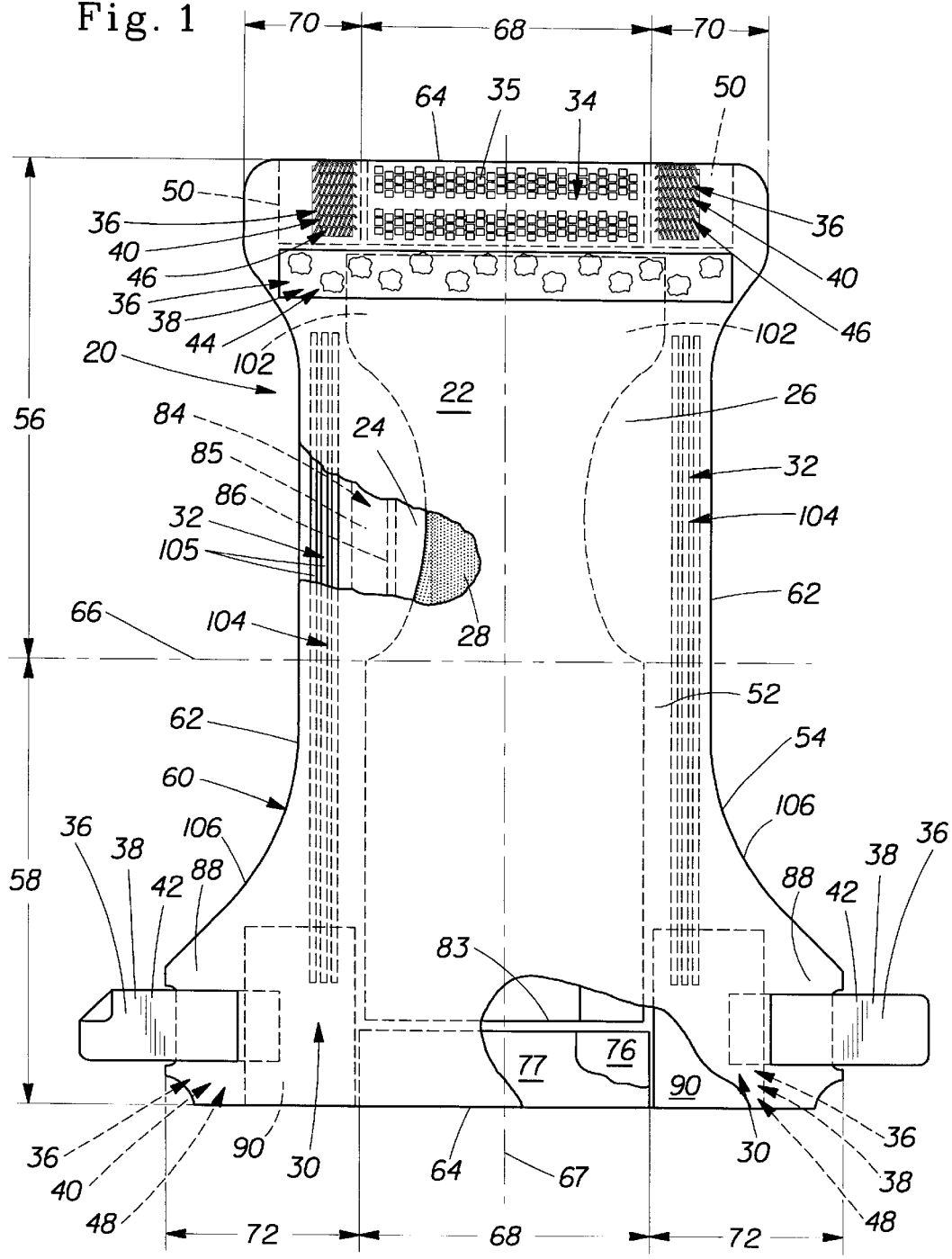
FIG. 1 is schematically showing a baby diaper as an example for an absorbent article.

FIG. 1 is a plan view of an embodiment of an absorbent article of the invention which is a diaper.

The diaper is shown in FIG. 1 in its flat-out, uncontracted state (i.e. with elastic induced contraction pulled out except in the side panels wherein the elastic is left in its relaxed condition) with portions of the structure being cut-away to more clearly show the construction of the diaper 20 and with the portion of the diaper 20 which faces away from the wearer, the outer surface 52, facing the viewer. As shown in FIG. 1, the diaper 20 comprises a containment assembly 22 preferably comprising a liquid pervious topsheet 24, a liquid impervious backsheet 26 joined with the topsheet 24, and an absorbent core 28 positioned between the topsheet 24 and the backsheet 26; elasticised side panels 30; elasticised leg cuffs 32; an elastic waist feature 34; and a closure system comprising a dual tension fastening system generally multiply designated as 36. The dual tension fastening system 36 preferably comprises a primary fastening system 38 and a waist closure system 40. The primary fastening system 38 preferably comprises a pair of securement members 42 and a landing member 44. The waist closure system 40 is shown in FIG. 1 to preferably comprise a pair of first attachment components 46 and a second attachment component 48. The diaper 20 also preferably comprises a positioning patch 50 located subjacent each first attachment component 46.

The diaper 20 is shown in FIG. 1 to have an outer surface 52 (facing the viewer in FIG. 1), an inner surface 54 opposed to the outer surface 52, a first waist region 56, a second waist region 58 opposed to the first waist region 56, and a periphery 60 which is defined by the outer edges of the diaper 20 in which the longitudinal edges are designated 62 and the end edges are designated 64. The inner surface 54 of the diaper 20 comprises that portion of the diaper 20 which is positioned adjacent to the 20 wearer's body during use (i.e. the inner surface 54 generally is formed by at least a portion of the topsheet 24 and other components joined to the topsheet 24). The outer surface 52 comprises that portion of the diaper 20 which is positioned away from the wearer's body (i.e. the outer surface 52 generally is formed by at least a portion of the backsheet 26 and other components joined to the backsheet 26). The first waist region 56 and the second waist region 58 extend, respectively, from the end edges 64 of the periphery 60 to the lateral centerline 66 of the diaper 20. The waist regions each comprise a central region 68 and a pair of side panels which typically comprise the outer lateral portions of the waist regions. The side panels positioned in the first waist region 56 are designated 70 while the side panels in the second waist region 58 are designated 72. While it is not necessary that the pairs of side panels or each side panel be identical, they are preferably mirror images one of the other. The side panels 72 positioned in the second waist region 58 can be elastically extensible in the lateral direction (i.e. elasticized side panels 30). (The lateral direction (x direction or width) is defined as the direction parallel to the lateral centerline 66 of the diaper 20; the longitudinal direction (y direction or length) being defined as the direction parallel to the longitudinal centerline 67; and the axial direction (Z direction or thickness) being defined as the direction extending through the thickness of the diaper 20).

FIG. 1 shows a specific of the diaper 20 in which the topsheet 24 and the backsheet 26 have length and width dimensions generally larger than those of the absorbent core 28. The topsheet 24 and the backsheet 26 extend beyond the edges of the absorbent core 28 to thereby form the periphery 60 of the diaper 20. The periphery 60 defines the outer perimeter or, in other words, the edges of the diaper 20. The periphery 60 comprises the longitudinal edges 62 and the end edges 64.

The containment assembly 22 of the diaper 20 is shown in FIG. 1 as comprising the main body (chassis) of the diaper 20. The containment assembly 22 comprises at least an absorbent core 28 and preferably an outer covering layer comprising the topsheet 24 and the backsheet 26. When the absorbent article comprises a separate holder and a liner, the containment assembly 22 generally comprises the holder and the liner (i.e. the containment assembly 22 comprises one or more layers of material to define the holder while the liner comprises an absorbent composite such as a topsheet, a backsheet, and an absorbent core). For unitary absorbent articles, the containment assembly 22 comprises the main structure of the diaper with other features added to form the composite diaper structure. Thus, the containment assembly 22 for the diaper 20 generally comprises the topsheet 24, the backsheet 26, and the absorbent core 28.

While each elastizised leg cuff 32 may be configured so as to be similar to any of the leg bands, side flaps, barrier cuffs, or elastic cuffs described above, it is preferred that each elasticized leg cuff 32 comprise at least an inner barrier cuff 84 comprising a barrier flap 85 and a spacing elastic member 86 such as described in the above-referenced U.S. Pat. No. 4,909,803. In a preferred embodiment, the elastisized leg cuff 32 additionally comprises an elastic gasketing cuff 104 with one or more elastic strands 105, positioned outboard of the barrier cuff 84 such as described in the above-references U.S. Pat. No. 4,695,278.

The diaper 20 may further comprise an elastic waist feature 34 that provides improved fit and containment. The elastic waist feature 34 at least extends longitudinally outwardly from at least one of the waist edges 83 of the absorbent core 28 in at least the central region 68 and generally forms at least a portion of the end edge 64 of the diaper 20. Thus, the elastic waist feature 34 comprises that portion of the diaper at least extending from the waist edge 83 of the absorbent core 28 to the end edge 64 of the diaper 20 and is intended to be placed adjacent the wearer's waist. Disposable diapers are generally constructed so as to have two elastic waist features, one positioned in the first waist region and one positioned in the second waist region. While a disposable diaper of the present invention can be constructed with a single elastic waist feature encircling the wearer or having a bolstering waist feature with rear elastics only, the discussion regarding the elastic waist feature will focus on diapers having a pair of elastic waist features, at least one, and preferably both, being constructed according to the present invention. Further, while the elastic waist feature or any of its constituent elements can comprise a separate element affixed to the containment assembly 22 of the diaper 20, the elastic waist feature 34 will be described with respect to a preferred embodiment in which the elastic waist feature 34 is constructed as an extension of other elements of the diaper such as the backsheet 26 or the topsheet 24, preferably both the backsheet 26 and the topsheet 24.

The elastisized waist band 35 of the elastic waist feature 34 may comprise a portion of the topsheet 24, a portion of the backsheet 26 that has preferably been mechanically stretched and a bi-laminate material comprising an elastomeric member 76 positioned between the topsheet 24 and backsheet 26 and resilient member 77 positioned between backsheet 26 and elastomeric member 76.

This as well as other components of the diaper are given in more detail in WO 93/16669 which is incorporated herein by reference.

Figure 2:
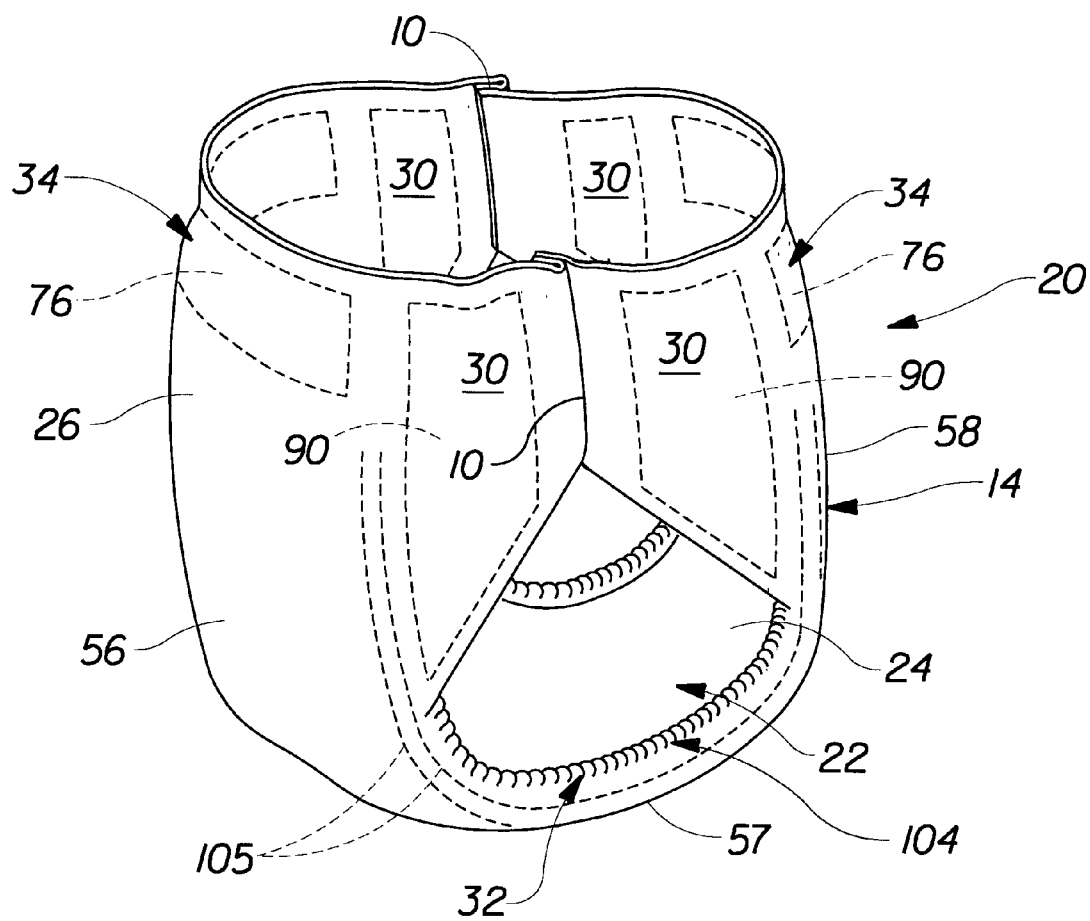
FIG. 2 is schematically showing a Pull up baby diaper as an example for an absorbent article.

FIG. 2 shows a further example for an absorbent article for which the present invention may be applied, namely a disposable pull-up diaper. The disposable pull-up diaper 20 comprise a chassis 21, side seems 23, and an absorbent assembly 22. The chassis 21 will have at least a front portion 56, a rear portion 58, a crotch portion 57, longitudinal side regions 88, and ear flaps 72 and will comprise an elastic ear flap member 90 operatively associated with each ear flap 72 to form a laminated ear flap which will be elastically activated by a mechanical stretching process which will be described in greater detail herein below. The absorbent assembly 22 is secured to the chassis 21.

The outer layer 26 is that portion of the chassis 21 which will form the exterior of the disposable pull-up diapers 20, i.e. face away from the wearer. The outer layer 26 is compliant, soft feeling, and non-irritating to the wearer's skin.

The inner layer 24 is that portion of the chassis 21 which will form the interior of the chassis 21, and will contact at least the waist and legs o.f the wearer. The inner layer is also compliant, soft feeling, and non-irritating to the wearer's skin.

The inner layer 24 is preferably positioned adjacent to the outer layer 26 and is preferably joined thereto by attachment means (not shown) such as those well known in the art. For example, the inner layer 24 may be secured to the outer layer 26 by a uniform continuous layer of adhesive, a patterned layer of adhesive, or an array of separate lines, spirals, or spots of adhesive.

According to an embodiment of the invention, the inner layer 24 and the outer layer 26 are indirectly joined together by directly joining them to the elastic ear flap members 90, elastic waste band members 76, and elastic strands 105 and are joined directly to each other in the areas extending beyond the elastic ear flap member 90, elastic waste band members 76, and elastic strands 45.

In a preferred embodiment, at least a portion of the chassis inner and outer layers 24, 26 will be subjected to mechanical stretching in order to provide a "zero strain" stretch laminate that forms the elastisized ear flaps 30. Thus, the inner and outer layers 24, 26 are preferably elongatable, most preferably drawable, but not necessarily elastomeric, so that the inner and outer layers 24, 26 will, upon mechanical stretching, be at least to a degree permanently elongated such that they will not fully return to their original undistorted configuration. In preferred embodiments, the inner and outer layers 24, 26 can be subjected to mechanical stretching without undue rupturing or tearing. Thus, it is preferred that the inner and outer layers 24, 26 have a low cross-machine direction (lateral direction) yield strength.

The chassis 21 of the disposable pull-up diapers 20 preferably further comprises elastisized leg. cuffs 32 for providing improved containment of liquids and other body exudates. Each elastisized leg cuff 32 may comprise several different embodiments for reducing the leakage of body exudates in the leg regions. While each elasticized leg cuff 32 may be configured so as to be similar to any of the leg bands, side flaps, barrier cuffs, or elastic cuffs described above, it is preferred that each elastisized leg cuff 32 comprise at least a side flap 104 and one or more elastic strands 105.

The chassis 21 of the disposable pull-up diapers 20 further preferably comprises an elastisized waistband 34 disposed adjacent the end edge 64 of the disposable pull-up-diapers 20 in at least the rear portion 58, and more preferably has an elasticised waistband 34 disposed in both the front portion 56 and the rear portion 58. The waistband of the disposable pull-up diapers 20 is that portion which is intended to be placed adjacent the wearer's waist. The elastisized waistband 34 provides a member that maintains a defined area coverage, contacts the wearer's waist, and is elastically extensible in at least the lateral direction so as to dynamically fit against the waist of the wearer and to dynamically conform to the waist of the wearer so as to provide improved fit. Thus, the waistband is generally that portion of the disposable pull-up diapers 20 extending from the end edge 64 of the disposable pull-up diapers 20 to at least the,waist edge 83 of the absorbent core 28. While the elastisized-waistband 34 can comprise a separate element affixed to the chassis 21 of the disposable pull-up diapers 20, the waistband is preferably an extension of other elements of the disposable pull-up diapers 20 such as the inner layer 24, the outer layer 26, or any combination of these elements and an elastomeric material joined thereto. Alternatively, the top sheet and the backsheet of the absorbent assembly 22, may extend beyond the edges of the absorbent core 28 and have an elastomeric material joined thereto to form an elasticised waistband. Disposable training-pants are often constructed so as to have two elastisized waistbands; one positioned in the front portion 56 and one positioned in the rear portion 58. The disposable pull-up diapers 20 at least has an. elastisized waistband 34 disposed in at least the central region 68 of the rear portion 58. Preferably another elastisized waistband is disposed on the front portion 56. Preferably both elastisized waistbands 34 are disposed between the elastisized ear flaps 30.

The elastisized. waste band 34 may be constructed in a number of different configurations. According to FIGS. 2 and 3, the elasticized waste band 34 comprises an elastic waste band member 76 interposed between the inner layer 24 and outer layer 26 and is operatively associated with either or both of the inner or outer layers 24, 26 together with the front portion 56 and rear portion 58 of the disposable pull-up diapers 20.

In a preferred embodiment, the chassis 21 comprises elastisized ear flaps 30 in the front portion 56 and the rear portion 58. The elastisized ear flaps 30 are unitary elements of the chassis, i.e. they are not separately manipulative elements secured to the chassis, but rather are formed from and are extensions of the chassis materials. The elastisized ear flaps 30 provide an elastically extensible feature that provides a more comfortable and contouring fit by initially conformably fitting the disposable garment to the wearer and sustaining this fit throughout the time of wear well past when the disposable garment has been loaded with exudates since the elastisized ear flaps allow the sides of the disposable garment to expand and contract.

Each ear flap 72 comprises that portion of the chassis 21 that extends laterally outwardly from and along the central region 68 of the chassis 21 to the longitudinal side region 88 of the chassis 21. The ear flap 72 generally extends longitudinally from the end edge 64 of the chassis 21 to the portions of the longitudinal edge 62 of the chassis 21 that forms the leg opening (this segment of the longitudinal edge 62 being designated as leg edge 106). In a preferred embodiment of the present invention, each ear flap is formed by the portions of the inner layer 24 and the outer layer 26 that extend beyond the central region 68 of the chassis 21.

In an embodiment of the present invention, the elastic ear flap members 90 are operatively associated with the chassis 21 in the ear flaps 72, preferably between the inner layer 24 and the outer layer 26, so that the elastic ear flap members 90 allow the elastisized ear flaps 30 to be elastically extensible in the lateral direction (laterally elastically extensible). As used herein, the term "elastically extensible" means a segment or portion of the chassis that will elongate in at least one direction (preferably the lateral direction for the ear flaps and the waistbands) when tensional forces (typically lateral tensional forces for the ear flaps and the waistbands) are applied, and will return to about its previous size and configuration when the tensional forces are removed. Generally, elastomeric materials useful in the present invention will contractively return to at least about 75% of their original configuration within about 5 seconds or less upon stretch and immediate release thereof (i.e. a "snappy" elastic).

Absorbent Core/Core structure

The absorbent core (28) should be generally compressible, conformable, non-irritating to the wearer's skin, and capable of absorbing and retaining liquids such as urine and other certain body exudates. As shown in FIG. 1, the absorbent core 28 has a garment surface ("lower" or "bottom" part), a body surface, side edges, and waist edges. The absorbent core might comprise a wide variety of liquid-absorbent or liquid handling materials commonly used in disposable diapers and other absorbent articles such as—but not limited to—comminuted wood pulp which is generally referred to as airfelt; meltblown polymers including coform; chemically stiffened, modified or cross-linked cellulosic fibers; tissue including tissue wraps and tissue laminates.

Examples for absorbent structures are described in U.S. Pat. No. 4,610,678 entitled "High-Density Absorbent Structures" issued to Weisman et al. on Sep. 9, 1986; U.S. Pat. No. 4,673,402 entitled "Absorbent Articles With Dual-Layered Cores" issued to Weisman et al. on Jun. 16, 1987; U.S. Pat. No. 4,888,231 entitled "Absorbent Core Having A Dusting Layer issued to Angstadt on Dec. 19, 1989; EP-A-0 640 330 of Bewick-Sonntag et al.; U.S. Pat. No. 5,180,622 (Berg et al.); U.S. Pat. No. 5,102,597 (Roe et al.); U.S. Pat. No. 5 387 207 (LaVon). Such structures might be adopted to be compatible with the requirements outline below for being used as the absorbent core 28.

The absorbent core 28 can be a unitary core structure, or it can be a combination of several absorbent structures, which in turn can consist of one or more sub-structures. Each of the structures or sub-structures can have an essentially two-dimensional extension (i.e. be a layer) or a three-dimensional shape.

Materials for Being Used in Absorbent Cores

The absorbent core for the present invention can comprise fibrous materials to form fibrous web or fibrous matrices.

Fibers useful in the present invention include those that are naturally occurring fibers (modified or unmodified), as well as synthetically made fibers. Examples of suitable unmodfiled/modified naturally occurring fibers include cotton, Esparto grass, bagasse, kemp, flax, silk, wool, wood pulp, chemically modified wood pulp, jute, rayon, ethyl cellulose, and cellulose acetate. Suitable synthetic fibers can be made from polyvinyl chloride, polyvinyl fluoride, polytetrafluoroethylene, polyvinylidene chloride, polyacrylics such as ORLON®, polyvinyl acetate, polyethylvinyl acetate, non-soluble or soluble polyvinyl alcohol, polyolefins such as polyethylene (e.g., PULPEX®) and polypropylene, polyamides such as nylon, polyesters such as DACRON® or KODEL®, polyurethanes, polystyrenes, and the like. The fibers used can comprise solely naturally occurring fibers, solely synthetic fibers, or any compatible combination of naturally occurring and synthetic fibers. The fibers used in the present invention can be hydrophilic, or can be a combination of both hydrophilic and hydrophobic fibers.

For many absorbent cores or core structures according to the present invention, the use of hydrophilic fibers is preferred. Suitable hydrophilic fibers for use in the present invention include cellulosic fibers, modified cellulosic fibers, rayon, polyester fibers such as polyethylene terephthalate (e.g., DACRON®), hydrophilic nylon (HYDROFIL®), and the like. Suitable hydrophilic fibers can also be obtained by hydrophilizing hydrophobic fibers, such as surfactant-treated or silica-treated thermoplastic fibers derived from, for example, polyolefins such as polyethylene or polypropylene, polyacrylics, polyamides, polystyrenes, polyurethanes and the like.

Suitable wood pulp fibers can be obtained from well-known chemical processes such as the Kraft and sulfite processes. It is especially preferred to derive these wood pulp fibers from southern soft woods due to their premium absorbency characteristics. These wood pulp fibers can also be obtained from mechanical processes, such as ground wood, refiner mechanical, thermomechanical, chemomechanical, and chemothermo-mechanical pulp processes. Recycled or secondary wood pulp fibers, as well as bleached and unbleached wood pulp fibers, can be used.

A desirable source of hydrophilic fibers for use in the present invention, especially for absorbent regions requiring both good fluid acquisition and distribution properties, is chemically stiffened cellulosic fibers. As used herein, the term "chemically stiffened cellulosic fibers" means cellulosic fibers that have been stiffened by chemical means to increase the stiffness of the fibers under both dry and aqueous conditions. Such means can include the addition of a chemical stiffening agent that, for example, coats and/or impregnates the fibers. Such means can also include the stiffening of the fibers by altering the chemical structure, e.g., by crosslinking polymer chains.

Polymeric stiffening agents that can coat or impregnate the cellulosic fibers include: cationic modified starches having nitrogen-containing groups (e.g., amino groups) such as those available from National Starch and Chemical Corp., Bridgewater, N.J., USA; latexes; wet strength resins such as polyamide-epichlorohydrin resin (e.g., Kymene® 557H, Hercules, Inc.

Wilmington, Del., USA), polyacrylamide resins described, for example, in U.S. Pat. No. 3,556,932 (Coscia et al), issued Jan. 19, 1971; commercially available polyacrylamides marketed by American Cyanamid Co., Stamford, Conn., USA, under the tradename Parez® 631 NC; urea formaldehyde and melamine formaldehyde resins, and polyethylenimine resins. A general dissertation on wet strength resins utilized in the paper art, and generally applicable herein, can be found in TAPPI monograph series No. 29. "Wet Strength in Paper and Paperboard", Technical Association of the Pulp and Paper Industry (New York, 1965).

These fibers can also be stiffened by chemical reaction. For example, crosslinking agents can be applied to the fibers that, subsequent to application, are caused to chemically form intrafiber crosslink bonds. These crosslink bonds can increase the stiffness of the fibers. While the utilizsation of intrafiber crosslink bonds to chemically stiffen the fiber is preferred, it is not meant to exclude other types of reactions for chemical stiffening of the fibers.

Fibers stiffened by crosslink bonds in individualised form (i.e., the individualised stiffened fibers, as well as process for their preparation) are disclosed, for example, in U.S. Pat. No. 3,224,926 (Bernardin), issued Dec. 21, 1965; U.S. Pat. No. 3,440,135 (Chung), issued Apr. 22, 1969; U.S. Pat. No. 3,932,209 (Chatterjee), issued Jan. 13, 1976; and U.S. Pat. No. 4,035,147 (Sangenis et al), issued Dec. 19,1989; U.S. Pat. No. 4,898,642d (Moore et al), issued Feb. 6, 1990; and U.S. Pat. No. 5,137,537 (Herron et al), issued Aug. 11, 1992.

In currently preferred stiffened fibers, chemical processing includes intrafiber crosslinking with crosslinking agents while such fibers are in a relatively dehydrated, defibrated (i.e., individualised), twisted, curled condition. Suitable chemical stiffening agents are typically monomeric crosslinking agents including, especially $C_2$–$C_9$ polycarboxylic acids such as citric acid.

Such stiffened fibers that are twisted and curled can be quantified by referencing both a fiber "twisted count" and a fiber "curl factor". As used herein, the term "twist count" refers to the number of twist nodes present in a certain length of fiber. Twist count is utilised as a means of measuring the degree to which a fiber is rotated about its longitudinal axis. The term "twist node" refers to a substantially axial rotation of 180° about the longitudinal axis of the fiber, wherein a portion of the fiber (i.e., the "node") appears dark relative to the rest of the fiber when viewed under a microscope with transmitted light. The twist node appears dark at locations wherein the transmitted light passes through an additional fiber wall due to the aforementioned rotation. The distance between nodes corresponds to an axial rotation of 180°. The number of twist nodes in a certain length of fibers (i.e., the twist count) is directly indicative of the degree of fiber twist, which is a physical parameter of the fiber. The procedures for determining twist nodes and total twist count are described in U.S. Pat. No. 4,898,642.

Such stiffened fibers will further have an average dry fiber twist count of at least about 2.7, preferably at least about 4.5 twist, nodes per millimetre. Furthermore, the average wet fiber twist count of these fibers should preferable be at least about 1.8, preferably at least about 3.0, and should also preferably be at least about 0.5 twist nodes per millimeter less than the average dry fiber twist count. Even more preferably, the average dry fiber twist count should be at least about 5.5 twist nodes per millimeter, and the average wet fiber twist count should be at least about 4.0 twist nodes per millimeter and should also be at least 1.0 twist nodes per millimeter less than its average dry fiber twist count. Most preferably, the average dry fiber twist count should be at least about 6.5 twist nodes per millimeter, and the average wet fiber twist count should be at least about 5.0 twist nodes per millimeter and should also be at least 1.0 twist nodes per millimeter less than the average dry fiber twist count.

In addition to being twisted, these preferred stiffened fibers are also curled. Fiber curl can be described as the fractional shortening of the fiber due to kinks, twists, and/or bends in the fiber. For the purposes of the present invention, fiber curl is measured in terms of a two dimensional plane. The extent of fiber curling can be quantified by referencing a fiber curl factor. The fiber curl factor, a two dimensional measurement of curl, is determined by viewing the fiber in a two dimensional plane. To determine curl factor, the projected length of the fiber as the longest dimension of a two dimensional rectangle encompassing the fiber, $L_R$, and the actual length of the fiber, $L_A$, are both measured. The fiber curl factor can then be calculated from the following equation:

Curl Factor=$(L_A/L_R)-1$.

An image analysis method that can be utilised to measure $L_R$ and $L_A$ is described in U.S. Pat. No. 4,898,642. Preferably the stiffened fibers will have a curl factor of at least about 0.30, and more preferably will have a curl factor of at least about 0.50.

These chemically stiffened cellulosic fibers have certain properties that make them particularly useful in certain absorbent structures according to the present invention, relative to unstiffened cellulosic fibers. In addition to being hydrophilic, these stiffened fibers have unique combinations of stiffness and resiliency.

In addition to or alternatively synthetic or thermoplastic fibers can comprised in the absorbent structures, such as being made from any thermoplastic polymer that can be melted at temperatures that will not extensively damage the fibers. Preferably, the melting point of this thermoplastic material will be less than about 190° C., and preferably between about 75° C. and about 175° C. In any event, the melting point of this thermoplastic material should be no lower than the temperature at which the thermally bonded absorbent structures, when used in absorbent articles, are likely to be stored. The melting point of the thermoplastic material is typically no lower than about 50° C.

The thermoplastic materials, and in particular the thermoplastic fibers, can be made from a variety of thermoplastic polymers, including polyolefins such as polyethylene (e.g., PULPEX®) and polypropylene, polyesters, copolyesters, polyvinyl acetate, polyamides, copolyamides, polystyrenes, polyurethanes and copolymers of any of the foregoing such as vinyl chloride/vinyl acetate, and the like. Suitable thermoplastic materials include hydrophobic fibers that have been made hydrophilic, such as surfactant-treated or silica-treated thermoplastic fibers derived from, for example, polyolefins such as polyethylene or polypropylene, polyacrylics, polyamides, polystyrenes, polyurethanes and the like. The surface of the hydrophobic thermoplastic fiber can be rendered hydrophilic by treatment with a surfactant, such as a nonionic or anionic surfactant, e.g., by spraying the fiber with a surfactant, by dipping the fiber into a surfactant or by including the surfactant as part of the polymer melt in producing the thermoplastic fiber. Upon melting and resolidification, the surfactant will tend to remain at the surfaces of the thermoplastic fiber. Suitable surfactants include nonionic surfactants such as Brij® 76 manufactured by ICI Americas, Inc. of Wilmington, Del., and various surfactants sold under Pegosperse® trademark by Glyco Chemical, Inc. of Greenwich, Conn. Besides nonionic surfactants, anionic surfactants can also be used. These surfactants can be applied to the thermoplastic fibers at levels of, for example, from about 0.2 to about 1 gram per square of centimeter of thermoplastic fiber.

Suitable thermoplastic fibers can be made from a single polymer (monocomponent fibers), or can be made from more than one polymer (e.g., bicomponent fibers). For example, "bicomponent fibers" can refer to thermoplastic fibers that comprise a core fiber made from one polymer that is encased within a thermoplastic sheath made from a different polymer. The polymer comprising the sheath often melts at a different, typically lower, temperature than the polymer comprising the core. As a result, these bicomponent fibers provide thermal bonding due to melting of the sheath polymer, while retaining the desirable strength characteristics of the core polymer.

Suitable bicomponent fibers for use in the present invention can include sheath/core fibers having the following polymer combinations: polyethylene/polypropylene, polyethylvinyl acetate/polypropylene, polyethylene/polyester, polypropylene/polyester, copolyester/polyester, and the like. Particularly suitable bicomponent thermoplastic fibers for use herein are those having a polypropylene or polyester core, and a lower melting copolyester, polyethylvinyl acetate or polyethylene sheath (e.g., DANAKLON®, CELBOND® or CHISSO® bicomponent fibers). These bicomponent fibers can be concentric or eccentric. As used herein, the terms "concentric" and "eccentric" refer to whether the sheath has a thickness that is even, or uneven, through the cross-sectional area of the bicomponent fiber. Eccentric bicomponent fibers can be desirable in providing more compressive strength at lower fiber thicknesses. Suitable bicomponent fibers for use herein can be either uncrimped (i.e. bent). Bicomponent fibers can be crimped by typical textile means such as, for example, a stuffer boy method or the gear crimp method to achieve a predominantly two-dimensional or "flat" crimp.

In the case of thermoplastic fibers, their length can vary depending upon the particular melt point and other properties desired for these fibers. Typically, these thermoplastic fibers have a length from about 0.3 to about 7.5 cm long, preferably from about 0.4 to about 3.0 cm long. The properties, including melt point, of these thermoplastic fibers can also be adjusted by varying the diameter (caliper) of the fibers. The diameter of these thermoplastic fibers is typically defined in terms of either denier (grams per 9000 meters) or decitex (grams per 10,000 meters dtex). Depending on the specific arrangement within the structure, suitable thermoplastic fibers can have a decitex in the range from well below 1 decitex, such as 0.4 decitex to about 20 decitex.

Said fibrous materials may be used in an individualised form when the absorbent article is being produced, and an airlaid fibrous structure is forrhed on the line. Said fibers may also be used as a preformed fibrous web or tissue. These structures are then delivered to the production of the article essentially in endless or very long form (e.g. on a roll, spool) and will then be cut to the appropriate size. This can be done on each of such materials individually before these are combined with other materials to form the absorbent core, of when the core itself is cut and said materials are co-extensive with the core.

There is a wide variety of making such webs or tissues, and such processes are very well known in the art.

With regard to fibers used for producing such webs, there is nearly no limitation in principle—though certain specific web forming and bonding processes might not be fully compatible with certain materials or fiber types.

When looking at individualised fibers as a starting material for making a web, these can be laid down in a fluid medium—if this is gaseous (air) such structures are generally referred to as dry-laid", if it is liquid such structures are generally referred to as "wet-laid". "Wet-laying" is broadly used to produce paper tissues with a wide range of properties. This term is most commonly used with cellulosic materials, however, also synthetic fibers can be included.

"Dry-laying" is broadly used for non-woven webs, and often the carding process can be used to form such webs. Also the commonly known "air-laid tissues" fall under this category.

A molten polymer can be extruded into fibers which then can be formed directly into a web (i.e. omitting the process step of making individual fibers which then are formed into a web in a separate process step). The resulting structures are commonly referred to as non-wovens of the meltblown type or—if fibers are significantly more drawn—spunbonded webs.

Further, webs can also be formed by combining one or more of the other formation technologies.

In order to give certain strength and integrity properties to the web structures, these are generally bonded. The most broadly used technologies are (a) chemical bonding or (b) thermo bonding by melting a part of the web such. For the latter, the fibers can be compressed, resulting in distinct bonding points, which, for example for nonwoven materials, can cover a significant portion of the total area, values of 20% are not uncommon. Or—particularly useful for structures where low densities are desired—"air-through" bonding can be applied, where parts of the polymers e.g. the sheath material of a BiCo-fibers are molten by means of heated air passing through the (often air-laid) web.

After the webs are formed and bonded, these can be further treated to modify specific properties. This can be—as one of many possible examples—additional surfactant to render hydrophobic fibers more hydrophilic, or vice versa. Also, post formation mechanical treatment, such as disclosed in EP application 96108427.4 can be used to impart particularly useful properties to such materials.

In addition or alternatively to fibrous webs, the absorbent cores may comprise other porous materials, such as foams. Preferred foams are open-celled absorbent polymeric foam materials as being derived by polymerising a High Internal Phase Water-in-Oil Emulsion (hereafter referred to a HIPE). Such polymeric foams may be formed to provide the requisite storage properties, as well as the requisite distribution properties.

HIPE-derived foams which provide both the requisite distribution and storage properties for use herein are described in copending U.S. patent application Ser. No. 08/563,866 (DesMarais et al.), filed Nov. 25, 1995 (hereafter referred to as "'866 application"), the disclosure of which is hereby incorporated by reference; copending U.S. patent application Ser. No. 08/542,497, filed Oct. 13, 1995 (Dyer et al.); U.S. Pat. No. 5,387,207 (Dyer et al.), issued Feb. 7, 1995; and U.S. Pat. No. 5,260,345 (DesMarais et al.), issued Nov. 9, 1993; the disclosure of each of which is hereby incorporated by reference.

Polymeric foams useful in the present invention are those which are relatively open-celled. This means the individual cells of the foam are in complete, unobstructed communication with adjoining cells. The cells in such substantially open-celled foam structures have intercellular openings or "windows" that are large enough to permit ready fluid transfer from one cell to the other within the foam structure.

These substantially open-celled foam structures will generally have a reticulated character with the individual cells being defined by a plurality of mutually connected, three dimensionally branched webs. The strands of polymeric material making up these branched webs can be referred to as "struts." Open-celled foams having a typical strut-type structure are shown by way of example in the photomicrographs of FIGS. 1 and 2 in the '866 application. As used herein, a foam material is "open-celled" if at least 80% of the cells in the foam structure that are at least 1 micro meter in size are in fluid communication with at least one adjacent cell.

In addition to being open-celled, these polymeric foams are sufficiently hydrophilic to permit the foam to absorb aqueous fluids in the amounts specified hereafter. The internal surfaces of the foam structures are rendered hydrophilic by residual hydrophilizing surfactants left in the foam structure after polymerization, or by selected post-polymerization foam treatment procedures.

The polymeric foams can be prepared in the form of collapsed (i.e. unexpanded), polymeric foams that, upon contact with aqueous fluids, expand and absorb such fluids. See, for example, copending U.S. patent application Ser. No. 08/563,866 and U.S. Pat. No. 5,387,207. These collapsed polymeric foams are usually obtained by expressing the water phase from the polymerized HIPE foam through compressive forces, and/or thermal drying and/or vacuum dewatering. After compression, and/or thermal drying/vacuum dewatering, the polymeric foam is in a collapsed, or unexpanded state. Non-collapsible foams, such as those described copending U.S. patent application Ser. No. 08/542,497 and U.S. Pat. No. 5,260,345 are also useful as the distribution material.

Superabsorbent Polymers or Hydrogels

Optionally, and often preferably, the absorbent structures according to the present invention can comprise Superabsorbent polymers, or hydrogels. The hydrogel-forming absorbent polymers useful in the present invention include a variety of substantially water-insoluble, but water-swellable polymers capable of absorbing large quantities of liquids. Such polymer materials are also commonly referred to as "hydrocolloids", or "superabsorbent" materials. These hydrogel-forming absorbent polymers preferably have a multiplicity of anionic, functional groups, such as sulfonic acid, and more typically carboxy, groups. Examples of polymers suitable for use herein include those which are prepared from polymerisable, unsaturated, acid-containing monomers.

Some non-acid monomers can also be included, usually in minor amounts, in preparing the hydrogel-forming absorbent polymers herein. Such non-acid monomers can include, for example, the water-soluble or water-dispersible esters of the acid-containing monomers, as well as monomers that contain no carboxylic or sulfonic acid groups at all. Examples for such well known materials are described e.g. in U.S. Pat. No 4,076,663 (Masuda et al), issued Feb. 28, 1978, and in U.S. Pat. No. 4,062,817 (Westerman), issued Dec. 13, 1977.

Hydrogel-forming absorbent polymers suitable for the present invention contain carboxy groups. These polymers include hydrolyzed starch-acrylonitrile graft copolymers, partially neutralized starch-acrylonitrile graft copolymers, starch-acrylic acid graft copolymers, partially neutralized starch-acrylic acid graft copolymers, saponified vinyl acetate-acrylic ester copolymers, hydrolyzed acrylonitrile or acrylamide copolymers, slightly network crosslinked polymers of any of the foregoing copolymers, partially neutralized polyacrylic acid, and slightly network crosslinked polymers of partially neutralized polyacrylic acid. These polymers can be used either solely or in the form of a mixture of two or more different polymers. Examples of these polymer materials are disclosed in U.S. Pat. No. 3,661,875, U.S. Pat. No. 4,076,663, U.S. Pat. No. 4,093,776, U.S. Pat. No. 4,666,983, and U.S. Pat. No. 4,734,478.

Most preferred polymer materials for use in making hydrogel-forming particles are slightly network crosslinked polymers of partially neutralized polyacrylic acids and starch derivatives thereof. Most preferably, the hydrogel-forming particles comprise from about 50 to about 95%, preferably about 75%, neutralized, slightly network crosslinked, polyacrylic acid (i.e. poly (sodium acrylate-lacrylic acid)).

As described above, the hydrogel-forming absorbent polymers are preferably slightly network crosslinked. Network crosslinking serves to render the polymer substantially water-insoluble and, in part, determines the absorptive capacity and extractable polymer content characteristics of the precursor particles and the resultant macrostructures. Processes for network crosslinking the polymers and typical network crosslinking agents are described in greater detail in the herein before-referenced U.S. Pat. No. 4,076,663, and in DE-A-4020780 (Dahmen).

The superabsorbent materials can be used in particulate form or in fibrous form and may also be combined other elements to form preformed structures.

Whilst the individual elements have been disclosed separately, and absorbent structure or substructure can be made by combining one or more of these elements.

Without intending a limiting effect, the following describes suitable combinations:

Particular Superabsorbent polymer (SAP) mixed with cellulosic or other fibers. The basic principle is well established and known, however, upon attempting to reduce thinness of the articles, higher and higher ratios of weight of SAP to fibers have been employed recently. Within this scope, combination of the SAP with binders such as hot-melt adhesives (such as disclosed in EP-A-0.695.541) or with meltable polymeric material (such as PE particles) can be a suitable tool to immobilise the SAP;

SAP forming a substructure by interparticle crosslinks;

Fibrous SAP being mixed with other fibers, or forming a fibrous SAP web;

Foam structures comprising differing in pore sizes etc.

Improved Absorbent Articles

After having described absorbent articles and suitable materials, structures, components or sub-components in general terms, the following will describe the specific features according to the present invention. Thereby, focus is put on describing the handling of urine discharges of the respective wearers, and the resulting urine handling requirement for the absorbent structures.

It should be noted, however, that the same fluid handling mechanisms apply to other primarily water based discharges, such as very low viscosity faeces or menstrual fluids.

Regions of Absorbent Articles

Generally, absorbent hygienic articles are intended for being worn around the lower end of the body torso. It is an essential design feature of these articles to cover the regions of the body where the discharges occur ("discharge regions"), which extend around the respective body openings. The respective zones of the absorbent article covering the discharge regions are correspondingly referred to as "loading zones". Thus during use, the articles are generally arranged on the wearer such that they extend (for a standing position of the wearer) from the crotch between the legs upwards, both in the front and the back of the wearer.

Generally, such articles have a length dimension exceeding their width dimension, whereby the article is worn such that the axis of the length dimension is aligned with the height direction of the wearer when standing, whilst the width direction of the article is aligned with a line extending from left to right of the wearer.

Because of the anatomy of the human wearer, the space between the legs of the wearer generally confines the space available for the article in this region. For good fit, an absorbent article should be designed such that it fits well in the crotch region. If the width of the article is excessively wide relative to the crotch width of the wearer, the article may be deformed, which might results in deteriorated performance, and reduced wearers comfort.

The point, where the article has its smallest width to fit best between the legs of the wearer then coincides with the point on the wearer, where the distance between the legs is the narrowest, and is—for the scope of the present invention—referred to as the "crotch point".

If the crotch point of an article is not obvious from its shape, it can be determined by placing the article on a wearer of the intended user group (e.g. a toddler) preferably in a standing position, and then placing an extensible filament around the legs in a figure eight configuration. The point in the article corresponding to the point of intersection of the filament is deemed to be the crotch point of the article and consequently also of the absorbent core being affixed within this article.

Whilst this crotch point of the article is often in the middle of the article (in longitudinal direction) this is not necessarily the case. It can very well be, that the part of the article which is intended to be worn in the front is smaller than the back (or rear) part—either in its length dimension, or width, or both, or surface area. Also, the crotch point does not need to be positioned in the middle of the absorbent core, in particular when the absorbent core is not placed longitudinally centred within the article.

The crotch region is the area surrounding the crotch point, so as to cover the respective body openings, respectively discharge regions. Unless otherwise mentioned, this region extends over a length of 50% of the total core length (which, in turn is defined as the distance between the front and rear waist edges of the core, which might be approximated by straight lines perpendicular to the longitudinal centre line). If the crotch point is positioned in the middle of the article, then the crotch region starts (when counting from the front core edge) at 25% of total length and extends up to 75% of the total core length. Or, the front and the rear quarter of the length of the absorbent core do not belong to the crotch region, the rest does.

The crotch region length being 50% of the total absorbent core length has been derived for baby diapers, where it has been confirmed that this is a suitable means to describe the fluid handling phenomena. If the present invention is applied in articles having drastically different dimensions, it might become necessary to reduce these 50% (as in the case for Severe Incontinence articles) or to increase this ratio (as in the case for Ultra Light or Light Incontinence articles). In more general terms, this crotch region of the article should not extend much beyond the discharge region of the wearer.

If the crotch point is positioned offset from the mid-point of the article, the crotch region still covers 50% of the total article length (in longitudinal direction), however, not evenly distributed between front and back, but proportionally adjusted to this off-set.

As an example for an article having a total core length of 500 mm, and having a crotch point which is positioned centred, the crotch region will extend from 125 mm away from the front edge up to 375 mm away from front edge. Or, if the crotch point lies 50 mm offset towards the front core edge, (i.e. being 200 mm away from front core edge), the crotch region extends from 100 mm to 350 mm.

In general terms, for an article having a total core length of $L_c$, a crotch point being at a distance $L_{cp}$ away from the front core edge, and a crotch zone length of $L_{cz}$, the front edge of said crotch zone will be positioned at a distance $$L_{fecz}=L_{cp}*(1-L_{cz}/L_c).$$

For example the absorbent article can be a baby diaper, for being worn by toddlers (i.e. of about 12 to 18 kg baby weight) whereby the size of the article in the trade is generally referred to as MAXI size. Then the article has to be able to receive and retain both fecal materials and urine, whereas for the context of the present invention the crotch region has to be capable to primarily receive urine loadings.

The total area and size of the crotch region is—of course—also depending on the respective width of the absorbent core, i.e. if the core is narrower in the crotch region than outside the crotch region, the crotch region has a smaller area (surface) than the remaining area of the absorbent core.

Whilst it can be contemplated, that the boundaries between crotch region and the rest of the article can also be curvilinear, they are approximated within the present description to be straight lines, perpendicular to the longitudinal axis of the article.

The "crotch region" is further confined by the width of the core in this respective region, and the "crotch region area" by the surface as being defined by the crotch region length and the respective width.

As a complementary element to the crotch region, the absorbent core also comprises at least one but mostly two waist region(s), extending towards the front and/or the rear of the absorbent core outside the crotch region.

Design Capacity and Ultimate Storage Capacity

In order to be able to compare absorbent articles for varying end use conditions, or differently sized articles, the "design capacity" has been found to be a suitable measure.

For example, babies are representing a typical usage group, but even within this group the amount of urine loading, frequency of loading, composition of the urine will vary widely from smaller babies (new-born babies) to toddlers on one side, but also for example among various individual toddlers.

Another user group may be larger children, still suffering from a certain form of incontinence.

Also, incontinent adults can use such articles, again with a wide range of loading conditions, generally referred to as light incontinence ranging up to severe incontinence.

Whilst the man skilled in the art will readily be able to transfer the teaching to other sizes for further discussion, focus will be put on the toddler sized babies. For such user, urine loadings of up to 75 ml per voiding, with on an average of four voidings per wearing period resulting in a total loading of 300 ml, and voiding rates of 15 m/sec have been found to be sufficiently representative.

Henceforth, such articles being able to cope with such requirements should have the capability of picking up such amounts of urine, which will be referred to for the further discussion as "design capacity". These amounts of fluids have to be absorbed by materials which can ultimately store the bodily fluids, or at least the aqueous parts of these, such that minimal fluid, if any, is left on the surface of the article towards the wearers skin. The term "ultimate" refers in one respect to the situation as in the absorbent article at long wearing times, in the other respect to absorbent materials which reach their "ultimate" capacity when being equilibrated with their environment. This can be in such an absorbent article under real in-use conditions after long wearing times, or this also can be in a test procedure for pure materials or material composites. As many of the processes under consideration have asymptotic kinetic behavior, one skilled in the art will readily consider "ultimate" capacities to be reached when the actual capacity has reached a value sufficiently close to the asymptotic endpoint, e.g. relative to the equipment measurement accuracy.

As an absorbent article can comprise materials which are primarily designed to ultimately store fluids, and other materials which are primarily designed to fulfill other functions such as acquisition and/or distribution of the fluid, but may still have a certain ultimate storage capability, suitable core materials according to the present invention are described without attempting to artificially separate such functions. Nonetheless, the ultimate storage capacity can be determined for the total absorbent core, for regions thereof, for absorbent structures, or even sub-structures, but also for materials as being used in any of the previous.

As discussed in the above for varying the dimensions of the article, one skilled in the art will be able to readily adopt the appropriate design capacities for other intended user groups.

Profiling

An important element of the present invention is a specific arrangement of the total absorbent capacity across the various regions of the absorbent article, such that the fit of the absorbent article on the body of the wearer is still comfortable even when the article is loaded close to or at its Design Capacity.

This specific arrangement is essentially aiming at providing only very little ultimate storage capacity in the crotch region.

The capacity of a specific region can be determined by:
the basis weights of the absorbent material under consideration [expressed in grams of material per unit area];
the materials absorbent capacities [expressed in ml capacity per gram of material],
the area of said region, for the present discussion defined by the longitudinal dimension of the region and the respective (not necessarily constant) width along this dimension.

The first two factors can be combined to the basis capacity [expressed in ml per unit area].

If any of these parameter is not constant (namely the width, or basis weights or composition), one skilled in the art will readily be able to calculate the respective weighing factors or averages, such as by summarizing (or integrating) the varying parameter and dividing by the respective parameter it has been summarized over.

Hence, one way to express the requirement of little Ultimate Storage Capacity in the crotch region is by defining that the crotch region has a lower basis capacity than the remaining part of the absorbent structure.

Then, the basis capacity of the crotch region should be not more than 0.9 times the average basis capacity of the remaining parts of the absorbent core preferably less than 0.7 times. However, the most preferred design has an even further reduced basis capacity in the crotch region, even of less than 0.3 times of the capacity of the remaining parts of the absorbent core. The crotch region may have a uniform basis capacity or comprise subregions with varying basis capacities. In a specific preferred design, parts of the crotch region have essentially no ultimate storage basis capacity, and such parts may cover 50% of the crotch region area or more.

Another way to describe this requirement of having low absorbent capacity in the crotch region is by looking at lengthwise sectional regions of the absorbent core, such as sectioning the absorbent core into a front, middle or rear third, or a crotch region having 50% of the total core length and comparing this to the remaining core sections. The sectional ultimate fluid storage capacity of the crotch region should then be less than 49% of the ultimate storage capacity of the total absorbent core. More preferably for an even further improved fit when loaded, even less absorbent capacity in said crotch region is preferred, namely less than 41% of the total absorbent capacity, or even more preferred are less than 23%.

The ultimate storage capacity distribution profile can be determined by calculating it from materials in respective sections, or also measured for example by cutting a article into sections having a known length dimension and determining the absorbent capacity per section.

If, as often in modem absorbent articles, superabsorbent materials are used as an ultimate storage material, a further way to define the requirement of low absorbent capacity in the crotch region is via limiting the superabsorbent capacity in analogy to the just discussed total absorbent capacity, i.e. with having less than 49% of the superabsorbent capacity, preferably less than 41% and most preferably less than 23% in the crotch region.

Thus, the "reverse profiling" of the ultimate absorbent capacity can be achieved by two different, non-exclusive ways:

The first starts from a constant "basis capacity" throughout the absorbent article, and the profiling is achieved by shaping the article such that the crotch region has a smaller area than the remaining regions. Consequently, the lengthways "sectional capacities" will be higher for the sections outside the crotch region.

The seconds starts with reduced "basis capacity" in the "crotch region", which—even for a rectangularly shaped core—would provide less capacity in the crotch region.

Of course, combinations of the two options can further sharpen the profile.

In addition to the relocation of the absorbent capacity away from the crotch region, it can be desirable to not distribute the fluid storage capacity evenly between the front and rear parts. Rather, it can be preferred, to adjust the capacity distribution to the specific requirements of the wearers anatomy, and the most often occurring usage situation. For example, for baby diapers intended to be worn by active toddlers it is desirable to have less capacity in the front region than in the back region. Also for adult incontinence people, which sometimes can be bedridden, a rearward asymmetric ultimate storage capacity distribution may be beneficial (such as described in EP-A-0.692.232).

In a preferred embodiment of the invention for baby diapers, less than half of the ultimate storage capacity, more preferably less than one third of the ultimate storage capacity that is positioned outside of the crotch region in positioned forwardly, i.e. in the front waist region, and more than half of the ultimate storage capacity, preferably at least two thirds are positioned in the rear part of the article.

However, there is a further requirement implied by the above designs, namely providing good rewet perfomance. As has been described above, the loading zone of the absorbent article lies generally in the crotch zone. The liquid storage capacity is, however, preferably located outside the crotch region. Consequently, the discharged liquid has to be transported from the loading zone to the storage zone, either at sufficiently high fluid transport rates to exceed the fluid delivery to the article, or in combination with an intermediate fluid handling ability, but in any case without detrimentally impacting on the dryness of the article surface towards the wearer, such as can be measured by the post acqusition collagen rewet method.

After an insult, it is an essential functionality of the absorbent article to retain the discharged fluids firmly so as to avoid over-hydration of the skin of the wearer. If the absorbent article is not well functioning in this respect, liquid coming from the absorbent core back to the skin— also often called "rewet" —can have detrimental effects on the condition of the skin, which can for example be observed by skin irritations.

It has been found, that when submitted to the Post acquisition collagen rewet test as described herein, results of less than 180 mg provide acceptable performance, but that well performing products provide a performance of less than 80 mg, preferably less than 70 mg or even more preferably less 50 mg.

In order to achieve the required fluid transport and intermediate fluid storage properties, capillary transport is an often used mechanism. Such mechanism depend largely on the capillaries as formed. However, such transport not only needs to be able to overcome certain heights but also needs to have a sufficiently high fluid transport rate. Thus, suitable materials not only must be able to quickly reach required vertical heights such as in the vertical wicking test but also must transport sufficient amount of fluid to such heights. It has been found that certain useful materials transport fluid to a wicking height of 8.3 cm in less than 13 seconds, or wicking heights of 12.4 cm in less than 45 seconds. But not only the time to reach certain heights is important, but also the flux at 8.3 cm is preferably higher than 0.32 ml sec/cm2, or preferably more than 0.16 ml/sec/cm2 at a height of 12.4 cm.

These requirements as well as suitable materials to satisfy such requirements have been disclosed in EP application 96108427.4, further also disclosing the rewet andlor skin dryness and acquisition performance requirements. There, however, no consideration was made with regard to the fit aspects of a loaded article, hence the performance requirements have been achieved while using conventional capacity distribution profiles.

Preferably, articles have an acquisition rate of more than 3.5 ml/sec in the acquisition test as described herein, preferably more than 4.0 ml/sec, more preferably more than 4.2 mvsec for the first gush, or 0.5 ml/sec, preferably more than 0.6 mvsec, more preferably more than 0.7 mvsec in the fourth gush.

Test Procedures

General

All tests are carried out at about 22+/−2° C. and at 35+1−15% relative humidity. The synthetic urine used in the test methods is commonly known as Jayco SynUrine and is available from Jayco Pharmaceuticals Company of Camp Hill, Pa. The formula for the synthetic urine is: 2.0 g/l of KCl; 2.0 g/l of $Na_2SO_4$; 0.85 g/l of $(NH_4)H_2PO_4$; 0.15 g/l $(NH_4)H_2PO_4$; 0.19 g/l of $CaCl_2$; ad 0.23 g/l of $MgCl_2$. All of the chemicals are of reagent grade. The pH of the synthetic Urine is in the range of 6.0 to 6.4.

Vertical Wicking Test

The vertical wicking test is aiming at evaluating the time required for a fluid front to reach a certain height in a vertical arrangement, i.e. against gravity, as well as amount of fluid picked up by the material during this time.

The principle of this test is to place a sample onto a sample holder equipped with electrodes in form of pins, both functioning to fix the sample in a vertical position and to allow generation of an electrical timer signal. The reservoir of the fluid is positioned on a scale, such that the time dependency of the fluid pick up in the sample resulting from the vertical wicking can be monitored. Whilst not being essential to the test, the test is executed based on a commercially available equipment, the EKOTESTER of Ekotec Industrietechnik GmbH, Ratingen, Germany, which also allowed electronic processing of the data.

Figure 3A:
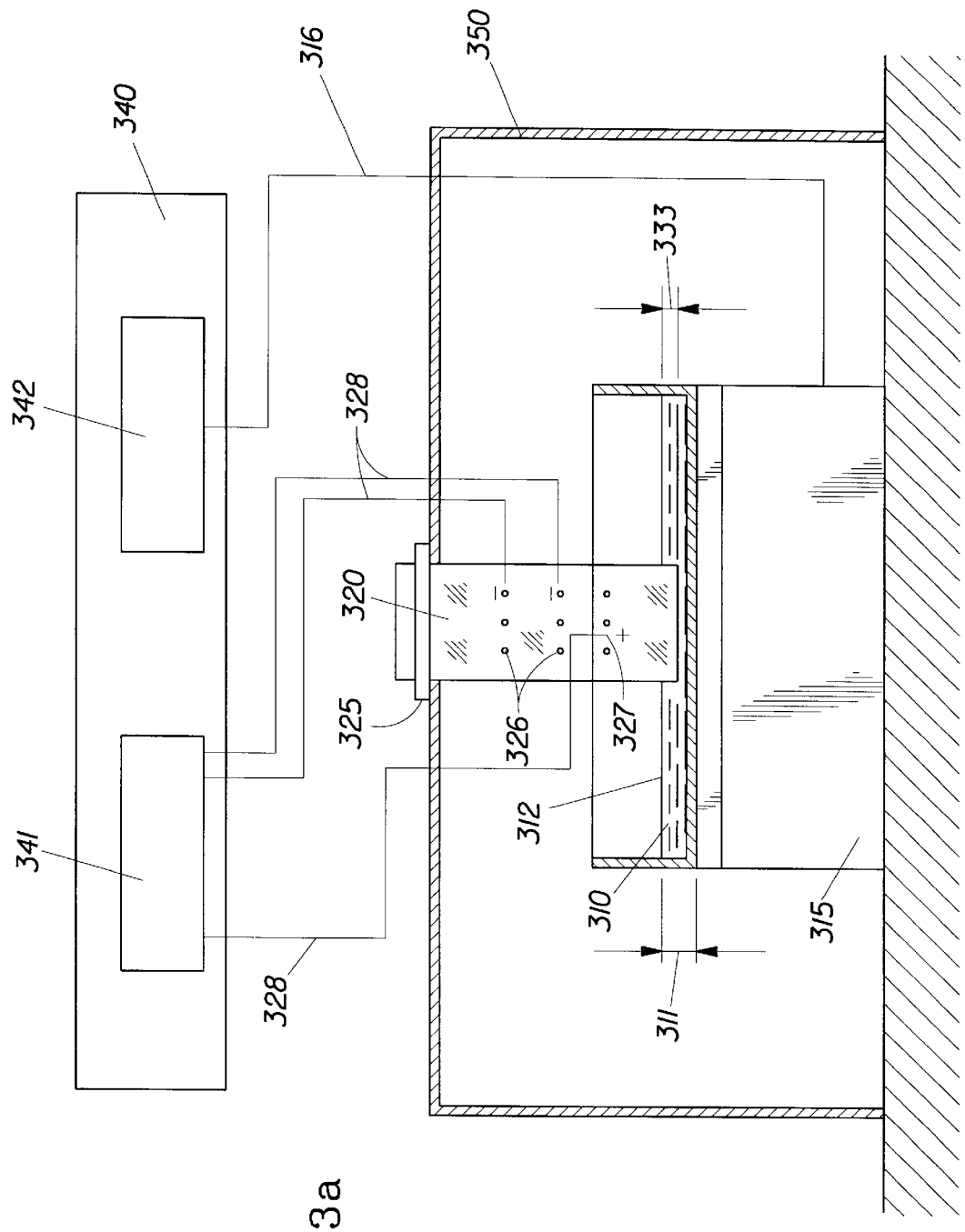
FIG. 3a is showing the test set up for the Vertical Wicking Test.
Figure 3B:
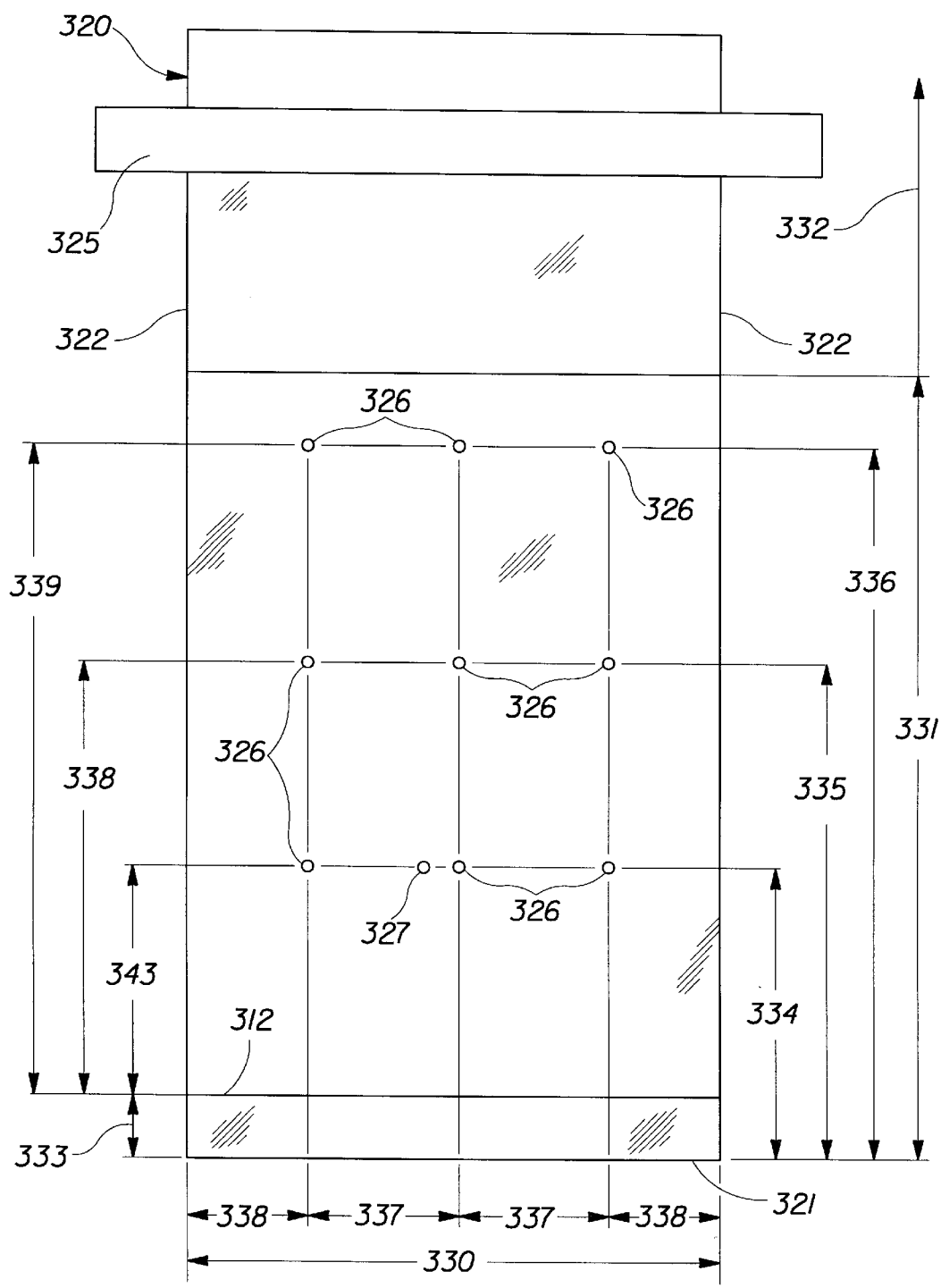

The test set up is schematically depicted in FIG. 3a and b.

The equipment is essentially made of perspex, and comprises a fluid reservoir (310) to hold 929 grams of test fluid at a liquid level height (311) of 17 mm and a sample holder (320). This reservoir is placed on a scale (315) with 0.1 g accuracy, such as manufactured by Mettler GmbH, type PM3000. Optionally, and indicated through the connection (316), this scale can be connected to an electronic data gathering device (342).

The sample holder (320) is essentially a perspex plate of a width (330) of 10 cm, a length (331) of 15 cm, and a thickness of about 5 mm (not shown). A fixation means (325) is extending beyond these dimensions in the direction (332) which becomes the upward direction during the test to ensure reproducible positioning in exactly vertical direction (i.e. direction of gravity) at a reproducible immersion depth (333) of the bottom edge (321) of the sample holder of 12 mm into the test fluid level in the reservoir (310) during the test. The sample holder (320) is further equipped with 9 cathode electrode pins (326), arranged in three rows in distances (334, 335, 336) of 56 mm, 95 mm, and 136 mm respectively from the bottom edge (321) of the sample holder. There are three electrodes in each of these rows, spaced evenly at distances (337) of 28 mm apart from each other, and the ones located to the longitudinal edge (322) being spaced at distances (338) of 22 mm away from these edges. The electrode pins have a length of about 10 mm, a diameter of about 1 mm, and are slightly sharpened at their end to ease application of the sample. The electrode pins are made of metal. A further anode electrode pin (327) is positioned 5 mm next to the middle cathode electrode pin of the bottom row. The anode (327) and the 9 cathodes (326) are connected (schematically indicated in FIG. 3a) (328) for two cathode pins and the anode pin) to a timing device (341) allowing to monitor the moment when the electric circuit between the anode and the individual cathodes is closed, such as by electrolyte test fluid in a wetted test sample which is positioned between these electrodes.

In contrast to the general procedures outlined above, this equipment is positioned and the test is executed in a temperature controlled hood set at 37° C. and not deviating more than 3° C. The test fluid is also prepared at 37° C. in a temperature controlled water bath for sufficient time to allow constant temperature of the fluid.

The test fluid is filled into the reservoir (310) to have the fluid surface (312) in level with the required height (311), e.g. by adding a predetermined amount of fluid, such as 927.3 gram plus/minus 1 gram.

The test specimen is equilibrated at laboratory conditions (see above), and put into the 37° C. environment just prior to the test. Also prior to the test, the caliper of the sample is measured as outlined below.

The test sample is cut to the size of 10 cm by 15 cm by any convenient means which avoids as much as possible compression effects at the cutting edges, such as with sample cutter such as from JDC Corporation, or sharp cutters like a scalpel or—less preferred—a sharp pair of scissors.

The test specimen is carefully placed onto the sample holder such that the edges coincide with the bottom and side edges (321 and 322) of the sample holder, i.e. such that it does not extend outside the sample holder plate. At the same time, the sample has to be in an essentially flat but unstressed arrangement, i.e. that it should neither form waves, not be in under mechanical tension. Care must be taken, that the sample has only direct contact to the electrode pins and is not contacting the perspex plate of the holder.

The sample holder (320) is then placed in a vertical position into the test fluid reservoir (310), such that the sample holder (320) as well as the test specimen are immersed exactly by a depth (333) of 12 mm into the fluid. Consequently, the electrodes will now have distances (343, 338, and 339) of 44 mm, 83 mm and 124 mm respectively to the fluid level (312), respectively. As the immersion of the sample holder does change the reading of the scale (315), this is tarred by an amount predetermined by inserting the sample holder without any sample, e.g. by 6 grams.

It will be acknowledged, that the positioning of the sample holder (320) and the test specimen in a non-tilted arrangement has to be very accurate on one side, but also quick, as the material will start sucking and wicking at first contact with the fluid. A frame (350) into which the sample holder can be readily inserted with the fixation means (325) is also a part of the EKOTESTER, but other means to achieve rapid and non-tilted fixation can be used.

The reading of the scale is monitored as a function of time immediately after positioning of the sample. It has been found advantageously to connect the scale to computerised equipment (340), such as being part of the EKOTESTER.

As soon as the fluid reaches the first row and closes the electrical connection between the anode (327) and the cathodes (326), these times can be recorded by any timing means, the timing unit (341) of the EKOTESTER being a convenient example. Whilst further data processing could be made with each of the three time values of one row, the further data refer to the average of all three electrodes per row, which generally did not spread more than approximately +/−5% from the average.

Thus, the data generated are:
the time dependent amount of fluid which is picked up by the sample after immersion, and
the time required for the fluid to reach certain heights.
From these, for each of the three heights two important values can be read and reported:

First, the times in seconds until the fluid front reaches the respective heights.

Second, the "cumulative flux" for each of the heights, by dividing
the amount of fluid picked up by the sample at the time when this height is reached
by this time
and by the cross-sectional area as defined by the caliper measurement and the 10 cm sample width.

Acquisition Test

Figure 4:
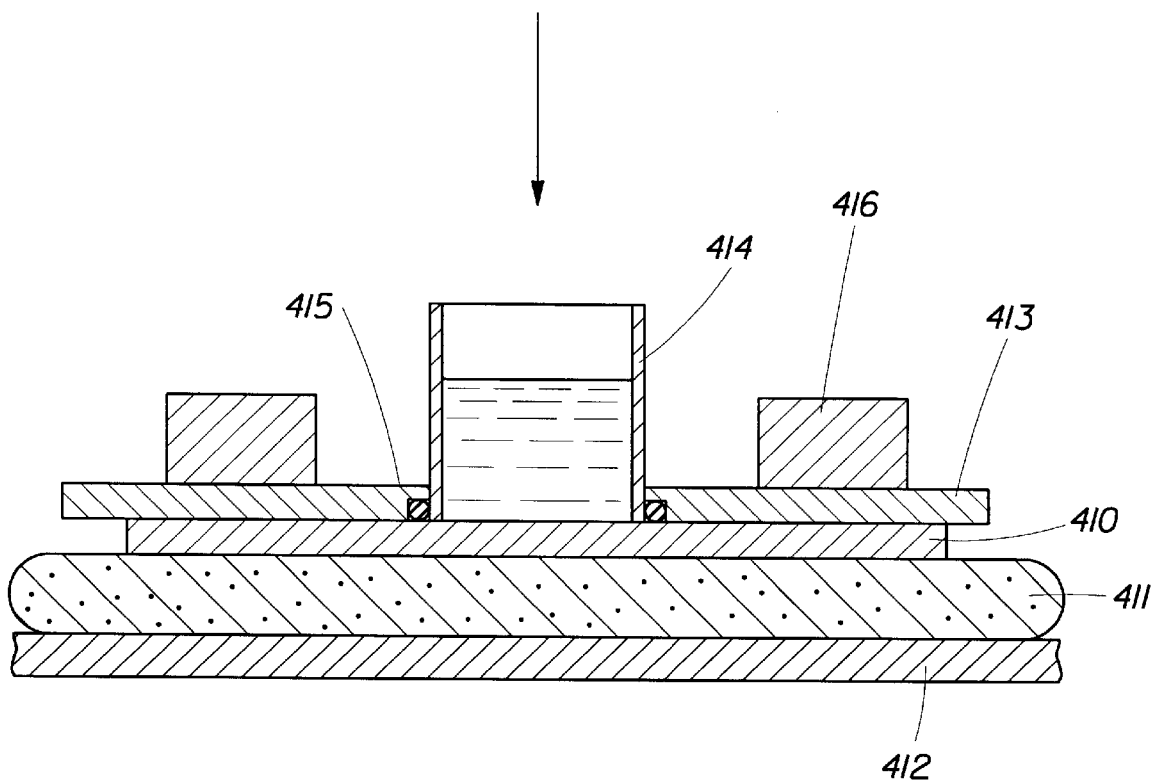
FIG. 4 is showing the test set up for the Acquisition Test.

Referring to FIG. 4, an absorbent structure (410) is loaded with a 75 ml gush of synthetic urine at a rate of 15 ml/s using a pump (Model 7520-00, supplied by Cole Parmer Instruments., Chicago, U.S.A.), from a height of 5 cm above the sample surface. The time to absorb the urine is recorded by a timer. The gush is repeated at precisely 5 minute gush intervals until the article is sufficiently loaded. Current test data are generated by loading four times.

The test sample, which can be a complete absorbent article or an absorbent structure comprising an absorbent core, a topsheet, and a backsheet, is arranged to lie flat on a foam platform 411 within a perspex box (only base 412 of which is shown). A perspex plate 413 having a 5 cm diameter opening in its middle is placed on top of the sample on the loading zone of the structure. Synthetic urine is introduced to the sample through a cylinder 414 fitted, and glued into the opening. Electrodes 415 are located on the lowest surface of the plate, in contact with the surface of the absorbent structure 410. The electrodes are connected to the timer. Loads 416 are placed on top of the plate to simulate, for example a baby's weight. A pressure of about 50 g cm-2 (0.7 psi) is achieved by positioning weights 416, e.g. for the commonly available MAXI size 20 kg.

As test fluid is introduced into the cylinder it typically builds up on top of the absorbent structure thereby completing an electrical circuit between the electrodes. The test fluid is transported from the pump to the test assembly by means of a tubing of about 8 mm diameter, which is kept filled with test fluid. Thus the fluid starts to leave the tubing essentially at the same time the pump starts operating. At this time, also the timer is started, and the timer is stopped when the absorbent structure has absorbed the gush of urine, and the electrical contact between the electrodes is broken.

The acquisition rate is defined as the gush volume absorbed (ml) per unit time(s). The acquisition rate is calculated for each gush introduced into the sample. Of particular interest in view of the current invention are the first and the last of the four gushes.

This test is primarily designed to evaluate products generally referred to as MAXI size products for a design capacity of about 300 ml, and having a respective Ultimate Storage Capacity of about 300 ml to 400 ml. If products with significantly different capacities should be evaluated (such as can be envisaged for adult incontinence products), the settings in particular of the fluid volume per gush should be adjusted appropriately to about 20% of the total article design capacity, and the deviation from the standard test protocol should be recorded.

Figure 5:
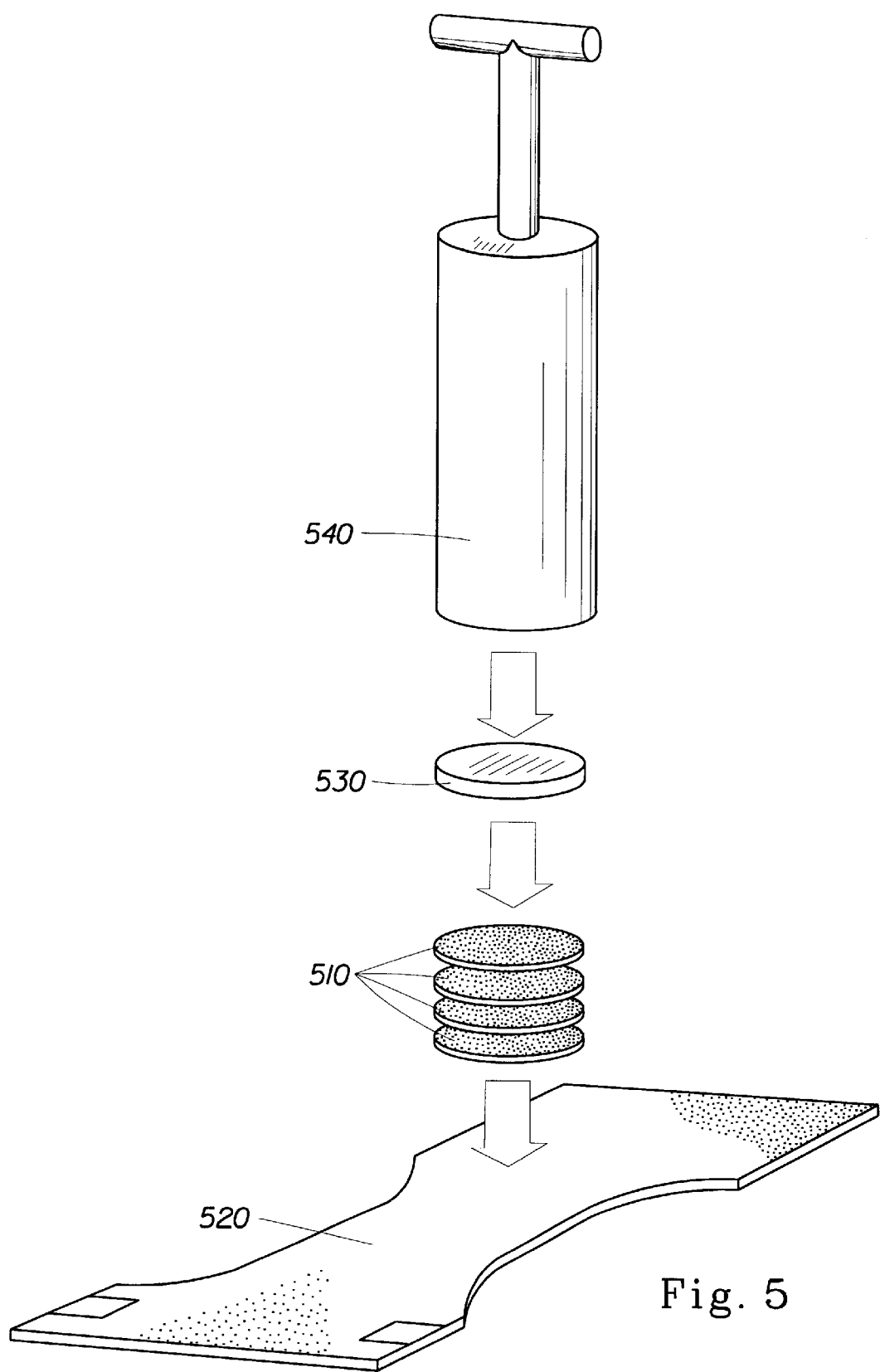
FIG. 5 is showing the test set up for the Post Acquisition Collagen Rewet Method.

Post Acquisition Collagen Rewet Method (refer to FIG. 5)

Before executing the test, the collagen film as purchased from NATURIN GmbH, Weinhein, Germany, under the designation of COFFI and at a basis weight of about 28 g/m$^2$ is prepared by being cut into sheets of 90 mm diameter e.g. by using a sample cutter device, and by equilibrating the film in the controlled environment of the test room (see above) for at least 12 hours (tweezers are to be used for all handling of the collagen film).

At least 5 minutes, but not more than 6 minutes after the last gush of the above acquisition test is absorbed, the cover plate and weights are removed, and the test sample (520) is carefully placed flat on a lab bench.

4 sheets of the precut and equilibrated collagen material (510) are weighed with at least one milligram accuracy, and then positioned centred onto the loading point of the article, and covered by perspex plate (530) of 90 mm diameter, and about 20 mm thickness. A weight (540) of 15 kg is carefully added (also centred). After 30+/−2 seconds the weight and perspex plate are carefully removed again, and the collagen films are reweighed.

The Post Acquisition Collagen Rewet Method result is the moisture pick up of the collagen film, expressed in mg.

It should be noted further, that this testing protocol can be adjusted easily according to specific product types, such as different baby diaper sizes, or adult incontinence articles, or catamenial articles, or by the variation in the type and amount of loading fluid, the amount and size of the absorbent material, or by variations in the applicable pressure. Having once defined these relevant parameters, such modifications will be obvious to one skilled in the art. When considering the results from the adjusted test protocol the products can easily be optimising these identified relevant parameter such as in a designed experiment according to standard statistical methods with realistic in use boundary conditions.

Fluid Distribution Test

The fluid distribution test is aiming at determining the amount of liquid picked up by a certain part of the absorbent article or core structure.

This test can be applied to articles loaded under controlled laboratory conditions, such as when executing other liquid handling capability assessment tests, e.g. the acquisition test as described above.

This test can also be applied to used articles such a when babies wear the diapers, load them under real use conditions, after which the articles are evaluated under appropriate hygienic conditions. The waiting time between the loading and the evaluation should not bee too long, though it has been found—at least for the designs as tested in the examples described below—the waiting time has only very little impact on the fluid distribution results.

In order to determine the fluid distribution in an absorbent structure or article, the loaded article is weighed and then laid out flat (optionally after cutting through the leg elastics so as to easy the flattening) and marked along its longitudinal axis in quarters. Then, the article is cut along lines perpendicular to the longitudinal line, whereby care must be taken to not squeeze out liquid. This can be best achieved by using a JCD paper cutter, or a scalpel.

Each segment is weighed, and the result rated to the total weight.

For articles having a strong profiling (i.e. different material weights in different sections), the total weight as well as the sectional weights can be adjusted by the dry weight of the article. To do so, the sectional weights can be determined for "sister diapers" (i.e. diapers made the same way, and—if done on a large scale production line—at about the same time as the tested diaper. If then the total article should have different weights, the sectional weights can be further adjusted according to this ratio, now assuming, that the deviations will be proportionally spread throughout the sections.

The result of the fluid distribution test is expressed in percentage of the total amount of fluid being present in certain sections, such as the crotch region.

Density/caliper/basis Weight Measurement

A specimen of a defined area such as by cutting with a sample cutter is weighed to at least 0.1% accuracy. Caliper is measured under an applied pressure of 550 Pa (0.08 psi) for an test area of 50 mm diameter. Basis weight as weight per unit area expressed in g/m2, caliper expressed in mm @ 550 Pa pressure, and density expressed in g/cm3 can be readily calculated.

Teabag Centrifuge CaDacity Test (TCC test)

Whilst the TCC test has been developed specifically for superabsorbent materials, it can readily be applied to other absorbent materials.

The Teabag Centrifuge Capacity test measures the Teabag Centrifuge Capacity values, which are a measure of the retention of liquids in the absorbent materials.

The absorbent material is placed within a "teabag", immersed in a 0.9% by weight sodium chloride solution for 20 minutes, and then centrifuged for 3 minutes. The ratio of the retained liquid weight to the initial weight of the dry material is the absorptive capacity of the absorbent material.

Two litres of 0.9% by weight sodium chloride in distilled water is poured into a tray having dimensions 24 cm×30 cm×5 cm. The liquid filling height should be about 3 cm.

The teabag pouch has dimensions 6.5 cm×6.5 cm and is available from Teekanne in Düsseldorf, Germany. The pouch is heat sealable with a standard kitchen plastic bag sealing device (e.g. VACUPACK2 PLUS from Krups, Germany).

The teabag is opened by carefully cutting it partially, and is then weighed. About 0.200 g of the sample of the absorbent material, accurately weighed to +/−0.005 g, is placed in the teabag. The teabag is then closed with a heat sealer. This is called the sample teabag. An empty teabag is sealed and used as a blank.

The sample teabag and the blank teabag are then laid on the surface of the saline solution, the timer is started immediately, and the teabags are submerged for about 5 seconds using a spatula to allow complete wetting (the teabags will float on the surface of the saline solution but are then completely wetted). After 20 minutes soaking time the sample teabag and the blank teabag are removed from the saline solution, and placed in a Bauknecht WS 130, Bosch 772 NZK096 or equivalent centrifuge (230 mm diameter), so that each bag sticks to the outer wall of the centrifuge basket. The centrifuge lid is closed, the centrifuge is started, and the speed increased quickly to 1,400 rpm. Once the centrifuge has been stabilized at 1,400 rpm the timer is started. After 3 minutes, the centrifuge is stopped.

The sample teabag and the blank teabag are removed and weighed separately.

The Teabag Centrifuge Capacity (TCC) for the sample of absorbent material is calculated as follows:

TCC=[(sample teabag weight after centrifuging)−(blank teabag weight after centrifuging)−(dry absorbent material weight)]÷(dry absorbent material weight).

Also, specific parts of the structures or the total absorbent articles can be measured, such as "sectional" cut outs, i.e. looking at parts of the structure or the total article, whereby the cutting is done across the full width of the article at determined points of the longitudinal axis of the article. In particular, the definition of the "crotch region" as described above allows to determine the "crotch region capacity". Other cut-outs can be used to determine a "basis capacity" (i.e. the amount of capacity contained in a unit area of the specific region of the article. Depending on the size of the unit area (preferably 2 cm by 2 cm) the defines how much averaging is taking place—naturally, the smaller the size, the less averaging will occur.

Ultimate Storage Capacity

In order to determine or evaluate the Ultimate Design Storage Capacity of an absorbent article, a number of methods have been proposed.

In the context of the present invention, it is assumed, that the Ultimate Storage Capacity of an article is the sum of the ultimate absorbent capacities of the individual elements or material. For these individual components, various well established techniques can be applied as long as these are applied consistently throughout the comparison. For example, the Tea Bag Centrifuge Capacity as developed and well established for superabsorbent polymers (SAP) can be used for such SAP materials, but also for others (see above).

Once the capacities for the individual materials are known, the total article capacity can be calculated by multiplying these values (in ml/g) with the weight of the material used in the article.

For materials having a dedicated functionality other than ultimate storage of fluids—such as acquisition layers and the like—the ultimate storage capacity can be neglected, either as such materials do in fact have only very low capacity values compared to the dedicated ultimate fluid storage materials, or as such materials are intended to not be loaded with fluid, and thus should release their fluid to the other ultimate storage materials.

Examples and Evaluation
Distribution Materials

For comparing various designs and material properties, two materials have been used to replace a conventional tissue, such as a high wet strength tissue of a basis weight of 22.5 g/m² as produced by Strepp, Kreuzau, Germany under reference NCB. Typical liquid transport properties for such tissues are listed in Table 1.

First, a high flux distribution material was evaluated (example 1.1), which has been made by starting from a wetlaid chemically bonded web having a basis weight of 150 gsm and a density of 0.094 g/cm3, consisting of a fiber blend of 90% by weight (of the fiber blend) of chemically-stiffened, twisted cellulose (CS), commercially available under the designation "CMC" from Weyerhaeuser Colo., US;

10% by weight (of the fiber blend) of eucalyptus type fibers, bonded by 2% per weight of fiber blend of a polyacrylamide-glyoxal resin marketed by Cytec Industries, West Patterson, N.J., USA, under the trade name Parez™ 631 NC.

This has then been subjected to a post formation treatment between two rolls at an overlap depth of the peaks of 0.2 mm with a width of a the teeth of 0.6 mm, being 1.0 mm spaced apart, as described in more detail in EP application 96108427.4.

A further thermally bonded wet laid material (example 1.2) has been made by using 60% of the chemically-stiffened twisted cellulose, 30% of said eucalyptus type fibers as used in above described chemically bonded distribution material, and 10% of eccentric, PE sheath/PET core BiCo fibers having a permanent hydrophilizer incorporated into the PE resin, produced by HOECHST CELANESE, US, under the designation Celbond® T255. After conventional wet-laying, this web has been thermally bonded by conventional air-through bonding technology by Ahlstrom Inc., US, at a basis weight of 150 gsm and a density of 0.11 g/cm³.

When being submitted to the Vertical Wicking Test as described above, the materials showed the results as shown in Table 1:

TABLE 1

|  | Example 1.1 | Example 1.2 | Example 1.3 |
| --- | --- | --- | --- |
| Wicking time in [sec] to reach |  |  |  |
| 8.3 cm | 13 sec | 45 | >210 |
| 12.4 cm | 45 sec | 165 | not reached |
| Flux. in [ml/sec/cm2] at |  |  |  |
| 8.3 cm | 0.32 | 0.06 | <0.02 |
| 12.4 cm | 0.16 | 0.04 | not reached |

Thus, Example 1.2 does provide improved performance over the conventional tissues of example 1.3, which however, still is significantly inferior to the ones of the particularly preferred material of example 1.1.

General Product Description

While the present invention is applicable to a broad range of products, the particular benefits have been exemplified in the context of baby diapers, and thereby for diapers intended for babies in the range of 8 to 18 kg, also called "MAXI" size. For such products, typical dimensions are the ones of PAMPERS BABY DRY PLUS MAXI/MAXI PLUS, such as marketed by Procter & Gamble throughout various countries in Europe:

|  | length (x-direction) | width (y-direction) |
| --- | --- | --- |
| total diaper | 499 mm | 430 mm |
| absorbent core | 438 mm | — |
| core ear width | — | 115 mm |
| core "crotch" | — | 102 mm |

During use, the design of these article is such that it fits essentially symmetrically when comparing the extension into the waist regions of the front to the back. The crotch point coincides with the "loading point", positioned (both for boy and girl babies) 4.9 cm towards the front waist region of the mid-sectional point of the article and 17 cm from front core edge. Consequently, the crotch region extends—when starting to count from the front waist end of the absorbent core (at 0 cm) towards the rear end (at 43.8 cm)—from 6.1 cm up to 27.8 cm.

The products exemplifying the present invention are generally derived from these commercially available product, and then modified as outlined in the specific examples. These products contain in their storage core about 20 g of conventional northern softwood airfelt, and about 10 g of superabsorbent material such a commercially available from Stockhausen GmbH, Germany under the trade name FAVOR SXM, type 100. The superabsorbent material has a theoretical capacity of 31 ml/g, which together with 4 ml/g for the airfelt provides a design capacity for such articles of about 390 ml. Additionally, the core comprises an "acquisition patch" overlying the storage core on a length of 25.4 cm, beginning from 28 cm off the front core edge towards the rear. This patch is made of air-laid chemically treated stiffened cellulosic material (CS) supplied by Weyerhaeuser Co., US under the trade designation of "CMC" functioning as an acquisition/distribution layer having a basis weight of about 295 g/m2. In the context of the present exemplification the ultimate storage capacity of these materials is set to zero, as the fluid is assumed to be removed from this acquisition/distribution layer so as this layer is ready for re-loading at repeated gushes (see above).

The core design is such that a mix of SAP and airfelt is overlying (in the direction towards the wearer) a thin layer of pure airfelt. The shape of the core is almost rectangular with a size of 438 mm by 115 mm, with a slightly narrowed width at the crotch point having a width of 102 mm. The mixed layer is profiled in basis weight, such that a lengthwise capacity distribution profile is approximately as follows:

| | |
|---|---|
| 1st quarter (front) | 140 ml |
| 2nd quarter | 130 ml |
| 3rd quarter | 70 ml |
| 4th quarter (rear) | 50 ml |

Fit Improvements

The first test aims at supporting the effect of redistribution of the storage capacity alone. To do so, a "fit study" has been conducted, whereby two products have been produced on pilot making facilities. First, a reference product was made aiming at replicating the marketed product as described above, differing from the latter by having no acquisition patch.

This product was compared to a "reverse profiled" design (example 2.1) differing only in that the capacity profile was differently phased, such that the capacity profile is as follows:

| | |
|---|---|
| 1st quarter (front) | 120 ml |
| 2nd quarter | 70 ml |
| 3rd quarter | 60 ml |
| 4th quarter (rear) | 140 ml |

These have been tested in a "fit study" whereby test products and reference products were evaluated by experienced mothers who provided a fit rating recored for a dry diaper and a diaper artificially loaded first with 150 ml, and then with 300 ml of synthetic urine.

For each product, the experienced mothers were questioned regarding the "overall" fit rating and the "fit between legs" rating for the various loadings.

The rating was categorised into a scale from 0 (poor) to 4 (excellent).

The products were placed among 17 randomly selected babies.

TABLE 2

| | Example 2.2 | Example 2.1 |
|---|---|---|
| Fit rating mother: | | |
| Overall fit | 2.6 | 2.0 |
| Fit between the legs: | | |
| when dry | 3.0 | 2.0 |
| at 150 ml | 2.9 | 1.9 |
| at 300 ml | 2.6 | 1.4 |

This clearly shows the poorer fit assessment of a conventionally profiled diaper in contrast to a reversed profiled one.
Performance Impact of Reverse Profiling (mixed cores)

However, consumers do not want to compromise performance for fit improvements. To assess the impact of the various designs on performance, products have been compared in laboratory testing for the highly relevant parameter of fluid acquisition performance and rewet.

For this test, products have been produced on a full scale pilot line, with one reference product replicating current market product design (example 3.1), except for having the acquisition patch being replaced by a thermally air-through bonded synthetic acquisition layer made by airlaying 63% eccentric PEIPP BiCo fibers (code ESEWA ex Danaklon AB, DK) together with 37% conventional southern softwood pulp into a web and airthrough bonding this to a density of 0.04 g/cm3, at a basis weight of 120 gsm (example 3.3). The next product was a combination of example 3.3 with the reverse capacity profile as described in example 2.1.

The third product (example 3.1) differed from this last in further comprising an thermally bonded wet laid material as described in example 1.2.

TABLE 3

| | Ex. 3.1 | Ex. 3.2 | Ex. 3.3 |
|---|---|---|---|
| Capacity distr. | reverse | reverse | crotch |
| Acquisition. material | air through bonded web (all) | | |
| Distr. mat. | wet laid air through | conventional tissue for both | |
| Fluid distr. [%] | | | |
| crotch | 58 | 55 | 79 |
| Acquisition test [ml/sec] | | | |
| 1st gush | 2.9 | 3.6 | 3.2 |
| 4th gush | 0.19 | 0.10 | 0.16 |
| Collagen rewet [mg] | | | |
| crotch | 268 | 283 | 262 |
| back | 25 | 72 | 12 |

These data demonstrate, that—while reverse profiling on its own does improve the fluid distribution by providing less capacity in the crotch zone—this benefit is compromised by poorer rewet performance, in particular in the rear of the article. Using an already improved fluid distribution material improves on this drawback without detrimentally impacting on the fluid distribution or the acquisition performance.

Distribution Material Impact in Conventionally Profiled Cores

The performance benefit of good distribution materials becomes further exemplified in reverse profile cores. To underline this effect, a conventional diaper (Example 4.2, same design as Example 2.2,) has been compared to Example 4.1, wherein the conventional tissue has been replaced by an improved distribution material (as described in Example 1).

TABLE 4

|  | Ex. 4.1 | Ex. 4.2 |
|---|---|---|
| Fluid distr. [%] | | |
| crotch | 91 | 88 |
| Acquisition test [ml/sec] | | |
| 1st gush | 3.9 | 4.8 |
| 4th gush | 0.59 | 0.82 |
| Collagen rewet [mg] | | |
| crotch | 60 | 53 |

Thus, the improved fluid distribution material does in fact improve performance, it does, however change the fluid distribution only to a very limited extend.

Layered Cores

The benefits of the present invention have been even further demonstrated in a test matrix whereby cores have been pilot line made without superabsorbent/fluff mixed cores, but rather with layered structures.

The overall design was same as in examples 3, whereby the absorbent core has been designed and made differently by replacing the homogeneously blended storage core by a rectangular absorbent structures with 15 g of superabsorbent powder being sandwiched between layers of either conventional tissue of the above described post formation treatment modified chemically bonded distribution material. The superabsorbent laminate had a width of 90 mm (centred) by using a glue spray lamination technique, a method as described in more detail in the above mentioned EP-A-0.695.541.

For two designs (referred to as "flat"), the laminate extended throughout the full length of the article, with a superabsorbent basis weight of 355 gsm.

For two reverse profile designs, the laminates extended both from front and rear core edge at a basis weight of 500 gsm over a length of 167 mm towards the crotch region, thus leaving about 130 mm in the middle section of the article superabsorbent free. As the latter is off-sent towards the front, a part of the crotch region is essentially superabsorbent free.

TABLE 5

|  | 5.1 | 5.2 | 5.3 | 5.4 |
|---|---|---|---|---|
| Capacity profile | rev. | rev. | flat | flat |
| Distr. material | high flux avg. | conv. avg. | high flux avg. | conv. avg. |
| Acquisition test [ml/sec] | | | | |
| 1st gush | 3.95 | 2.92 | 3.91 | 2.89 |
| 4th gush | 0.66 | 0.36 | 0.73 | 0.54 |
| Collagen rewet [µg] | | | | |
| crotch | 59 | 118 | 65 | 106 |
| back | | | | |
| Fluid distr. [%] | | | | |
| crotch | 56 | 58 | 70 | 73 |

This table further demonstrates the beneficial effect of good distribution materials on the performance of the article:

It further demonstrates, that—independent of tissue or high flux material—the fluid distribution is positively impacted by the reverse profile design. However, clearly, the rewet is majorly compromised for the tissue products.

The overall conclusion from these experiments can be summarised, that a preferred product has little ultimate storage capacity in the crotch zone, a good distribution material, preferably a high flux fluid distribution material, such that the product still exhibits good fluid handling performance as measured by acquisition and/or rewet values.

What is claimed is:

1. Absorbent article comprising an absorbent core comprising a crotch region and one or more waist regions,
   whereby said crotch region has a lower ultimate fluid storage capability than one or more waist regions together,
   characterized in that
      said article has a crotch region Post Acquisition Collagen Rewet Method value of less than 180 mg.

2. An absorbent article according to claim 1, wherein said article has a crotch region Post Acquisition Collagen Rewet Method value of less than 80 mg.

3. An absorbent article according to claim 2,
   wherein said article has a crotch region Post Acquisition Collagen Rewet Method value of less than 70 mg.

4. An absorbent article according to claim 3, wherein the article has a crotch region Post Acquisition Collagen Rewet Method value of less than 50 mg.

5. An absorbent article according to claim 1,
   wherein said crotch region has a sectional ultimate fluid storage capacity of less than 49% of the total core ultimate fluid storage capacity.

6. An absorbent article according to claim 5,
   wherein said crotch region has a sectional ultimate fluid storage sectional capacity of less than 41% of the total core ultimate fluid storage capacity.

7. An absorbent article according to claim 6,
   wherein said crotch region has a sectional ultimate fluid storage sectional capacity of less than 23% of the total core ultimate fluid storage capacity.

8. An absorbent article according to claim 1,
   further characterized in that
      the length of the crotch region is half of the length of the total absorbent core.

9. An absorbent article according to claim 1,
   further characterized in that it
      comprises an ultimate liquid storage material providing at least 80% of the total ultimate storage capacity of the absorbent core.

10. An absorbent article according to claim 9,
    further characterized in that
       said ultimate liquid storage material provides at least 90% of the total ultimate storage capacity of the absorbent core.

11. An absorbent article according to claim 1,
    further characterized in that
       said ultimate liquid storage material comprises superabsorbent polymers.

12. An absorbent article according to claim 1,
    further characterized in that
       said ultimate liquid storage material comprises no superabsorbent polymers.

13. An absorbent article according to claim 1,
    further characterized in that said ultimate liquid storage material comprises an open cell absorbent foam material.

14. An absorbent article according to claim 13, wherein said absorbent foam materials is derived from a high internal phase water-in-oil emulsion.

15. An absorbent article according to claim 1, further characterized in that at least 50% of the area of said crotch region contain essentially no ultimate storage capacity.

16. An absorbent article according to claim 1, further characterised in that less than 50% of said ultimate storage capacity are positioned forwardly from the crotch zone in the front half of the article, and more than 50% of said ultimate storage capacity are positioned in the rear half of the article.

17. An absorbent article according to claim 16, wherein less than 33% of said ultimate storage capacity are positioned forwardly from the crotch zone in the front half of the article, and more than 67% of said ultimate storage capacity are positioned in the rear half of the article.

18. An absorbent article according to claim 1, further characterised that the article has in said crotch region an Acquisition performance of at least 0.5 ml/sec for the fourth gush.

19. An absorbent article according to claim 1, wherein said crotch region comprises a material having a flux at 12.4 cm of more than 0.075 g/cm2/sec.

20. An absorbent artide according to claim 1, wherein said crotch region comprises a material obtainable by a post-formation treatment of a chemically bonded wet laid web comprising stiffened cellulosic fibres, eucalyptus type of fibres and and chemical binder resin.

21. An absorbent article comprising an absorbent core having an average ultimate fluid storage basis capacity, the absorbent core comprising a crotch region and one or more waist regions,
   whereby said crotch region has a lower ultimate fluid storage capability than one or more waist regions together,
   wherein said crotch region has an ultimate fluid storage basis capacity of less than 0.9 times the average ultimate fluid storage basis capacity of the absorbent core.

22. An absorbent article according to claim 21,
   wherein said crotch region has an ultimate fluid storage basis capacity of less than 0.7 times the average ultimate fluid storage basis capacity of the absorbent core.

23. An absorbent article according to claim 22,
   wherein said crotch region has an ultimate fluid storage basis capacity of less than 0.5 times the average ultimate fluid storage basis capacity of the absorbent core.

24. An absorbent article according to claim 23,
   wherein said crotch region has an ultimate fluid storage basis capacity of less than 0.3 times the average ultimate fluid storage basis capacity of the absorbent core.

* * * * *

UNITED STATES PATENT AND TRADEMARK OFFICE
CERTIFICATE OF CORRECTION

PATENT NO. : 6,278,037 B1
DATED : August 21, 2001
INVENTOR(S) : Gary D. Lavon et al.

It is certified that error appears in the above-identified patent and that said Letters Patent is hereby corrected as shown below:

Column 2,
Line 29, "(Bemardin)" should read -- (Bernardin) --.
Line 66, "somle holder fot" should read -- sample holder for --.

Column 3,
Line 29, "diaper" should read -- diaper 20 --.

Column 4,
Line 44, "elastizised" should read -- elasticized --.
Lines 50-51, "elastisized" should read -- elasticized --.

Column 5,
Line 45, "o.f" should read -- of --.

Column 6,
Line 10, "leg." should read -- leg --.
Line 22, "pull-up-diapers" should read -- pull-up diapers --.
Line 35, "the,waist" should read -- the waist --.
Line 55, "elasticized." should read -- elasticized --.

Column 8,
Line 12, "unmodfiled/modified" should read -- unmodified/modified --.

Column 9,
Line 17, "utilizsation" should read -- utilization --.
Line 59, "millimetre" should read -- millimeter --.

Column 15,
Line 39, "Whilst" should read -- While --.

Column 16,
Lines 36 and 66, "Whilst" should read -- While --.

Column 18,
Line 38, "modem" should read -- modern --.

UNITED STATES PATENT AND TRADEMARK OFFICE
CERTIFICATE OF CORRECTION

PATENT NO. : 6,278,037 B1
DATED : August 21, 2001
INVENTOR(S) : Gary D. Lavon et al.

It is certified that error appears in the above-identified patent and that said Letters Patent is hereby corrected as shown below:

Column 19,
Line 56, "andlor" should read -- and/or --.
Line 66, "0.6 mvsec" should read -- 0.6 mv/sec --.
Line 66, "0.7 mvsec" should read -- 0.7 mv/sec --.

Column 24,
Line 19, "CaDacity" should read -- Capacity --.

Column 28,
Line 26, "PEIPP" should read -- PE/PP --.

Column 32,
Lines 1 and 2, "fibres" should read -- fibers --.
Line 2, delete the second occurrence of "and".

Signed and Sealed this

Eighteenth Day of March, 2003

JAMES E. ROGAN
*Director of the United States Patent and Trademark Office*